US008280746B2

(12) United States Patent
Firminger et al.

(10) Patent No.: US 8,280,746 B2
(45) Date of Patent: *Oct. 2, 2012

(54) PERSONALIZED PLAN DEVELOPMENT

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 328 days.

This patent is subject to a terminal disclaimer.

(21) Appl. No.: 12/584,653

(22) Filed: Sep. 8, 2009

(65) Prior Publication Data
US 2011/0054939 A1 Mar. 3, 2011

Related U.S. Application Data

(63) Continuation-in-part of application No. 12/584,489, filed on Sep. 3, 2009.

(51) Int. Cl.
*G06Q 10/00* (2006.01)

(52) U.S. Cl. ..................................................... 705/1.1
(58) Field of Classification Search ....................... None
See application file for complete search history.

(56) References Cited

U.S. PATENT DOCUMENTS

| 4,853,854 A | 8/1989 | Behar et al. |
| 5,961,446 A | 10/1999 | Beller et al. |
| 6,338,044 B1 | 1/2002 | Cook et al. |
| 6,353,447 B1 | 3/2002 | Truluck et al. |
| 6,842,604 B1 | 1/2005 | Cook et al. |
| 7,587,368 B2 | 9/2009 | Felsher |
| 7,668,735 B2 | 2/2010 | Grace et al. |
| 7,702,685 B2 | 4/2010 | Shrufi et al. |
| 7,860,852 B2 | 12/2010 | Brunner et al. |
| 7,908,182 B1 | 3/2011 | Gupta |

(Continued)

OTHER PUBLICATIONS

U.S. Appl. No. 12/655,582, Firminger et al.

(Continued)

*Primary Examiner* — Michelle Le

(57) ABSTRACT

A computationally implemented method includes, but is not limited to: receiving a request for a personalized plan designed to facilitate an end user to achieve one or more target outcomes when one or more emulatable aspects indicated by the personalized plan are emulated, the request identifying at least a source user; acquiring source user data indicating a plurality of reported aspects associated with at least the source user in response to receiving the request; and developing the personalized plan by at least determining which of the plurality of reported aspects associated with the source user are relevant to the achievement of the one or more target outcomes. In addition to the foregoing, other method aspects are described in the claims, drawings, and text forming a part of the present disclosure.

42 Claims, 25 Drawing Sheets

U.S. PATENT DOCUMENTS

| | | | |
|---|---|---|---|
| 7,959,567 | B2 | 6/2011 | Stivoric et al. |
| 8,005,906 | B2 | 8/2011 | Hayashi et al. |
| 2002/0107707 | A1 | 8/2002 | Naparstek et al. |
| 2004/0015337 | A1 | 1/2004 | Thomas et al. |
| 2005/0197553 | A1 | 9/2005 | Cooper |
| 2005/0216300 | A1 | 9/2005 | Appelman et al. |
| 2006/0036619 | A1 | 2/2006 | Fuerst et al. |
| 2007/0088576 | A1 | 4/2007 | de Beus et al. |
| 2008/0091471 | A1 | 4/2008 | Michon et al. |
| 2008/0288425 | A1 | 11/2008 | Posse et al. |
| 2008/0294012 | A1 | 11/2008 | Kurtz et al. |
| 2009/0044113 | A1 | 2/2009 | Jones et al. |
| 2009/0070679 | A1 | 3/2009 | Shen et al. |
| 2009/0075242 | A1 | 3/2009 | Schwarzberg et al. |
| 2009/0076335 | A1 | 3/2009 | Schwarzberg et al. |
| 2009/0100469 | A1 | 4/2009 | Conradt et al. |
| 2009/0176526 | A1 | 7/2009 | Altman |
| 2009/0258710 | A1 | 10/2009 | Quatrochi et al. |
| 2009/0271247 | A1 | 10/2009 | Karelin et al. |
| 2009/0292814 | A1 | 11/2009 | Ting et al. |
| 2009/0299990 | A1 | 12/2009 | Setlur et al. |
| 2009/0313041 | A1* | 12/2009 | Eder .................................. 705/2 |
| 2009/0319288 | A1 | 12/2009 | Slaney et al. |
| 2009/0326981 | A1 | 12/2009 | Karkanias et al. |
| 2010/0063993 | A1 | 3/2010 | Higgins et al. |
| 2010/0114788 | A1 | 5/2010 | White et al. |
| 2010/0268830 | A1 | 10/2010 | McKee et al. |
| 2010/0281364 | A1 | 11/2010 | Sidman |
| 2010/0293247 | A1 | 11/2010 | McKee et al. |
| 2010/0305806 | A1 | 12/2010 | Hawley |
| 2011/0022602 | A1 | 1/2011 | Luo et al. |
| 2011/0179161 | A1 | 7/2011 | Guy et al. |
| 2011/0185020 | A1 | 7/2011 | Ramamurthy et al. |
| 2011/0252101 | A1 | 10/2011 | Davis et al. |

OTHER PUBLICATIONS

U.S. Appl. No. 12/655,581, Firminger et al.
U.S. Appl. No. 12/655,365, Firminger et al.
U.S. Appl. No. 12/655,250, Firminger et al.
U.S. Appl. No. 12/655,075, Firminger et al.
U.S. Appl. No. 12/653,972, Firminger et al.
U.S. Appl. No. 12/653,387, Firminger et al.
U.S. Appl. No. 12/653,386, Firminger et al.
U.S. Appl. No. 12/653,180, Firminger et al.
U.S. Appl. No. 12/653,117, Firminger et al.
U.S. Appl. No. 12/592,946, Firminger et al.
U.S. Appl. No. 12/592,944, Firminger et al.
U.S. Appl. No. 12/592,548, Firminger et al.
U.S. Appl. No. 12/592,544, Firminger et al.
U.S. Appl. No. 12/592,161, Firminger et al.
U.S. Appl. No. 12/592,075, Firminger et al.
U.S. Appl. No. 12/590,841, Firminger et al.
U.S. Appl. No. 12/590,600, Firminger et al.
U.S. Appl. No. 12/590,039, Firminger et al.
U.S. Appl. No. 12/590,027, Firminger et al.
U.S. Appl. No. 12/587,127, Firminger et al.
U.S. Appl. No. 12/587,018, Firminger et al.
U.S. Appl. No. 12/584,489, Firminger et al.
Chen, Jason; "You Can Soon Track Your Heart Rate with Your iPhone"; Gizmodo; Bearing a date of Oct. 9, 2009; p. 1; Creative Commons License; located at: http://gizmodo.com/5378340/you-can-soon-track-your-heart-rate-with-your-iphone; printed on Oct. 29, 2009.
Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the . . . ; printed on Nov. 25, 2009.
"Exercise Pro Software Active Care Version 5"; BioEX Systems, Inc.; bearing dates of 1995-2009; pp. 1-4; located at http://www.bioexsystems.com/ActiveCare.htm; printed on Dec. 17, 2009.
"Fitbit automatically tracks your fitness & sleep"; fitbit.com; bearing a date of 2009; pp. 1-2; located at http://www.fitbit.com; printed on Oct. 29, 2009.
Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919 . . . ; printed on Nov. 25, 2009.
Guez, Tomer; "Weight Loss Software, Food Diary, Exercise Tracker, and Medical Diary. 'The Food and Exercise Diary Software Version 6.0'"; bearing a date of Sep. 2009; pp. 1-17; located at http://www.weightlosssoftware.com/?ti=135&wn=2; printed on Dec. 17, 2009.
"Nutrition tracking software is critical for learning about foods and planning meals"; NutriCoach; bearing a date of Mar. 29, 2006; 6 total pgs.; located at http://www.nutricoach.net/diet_software.html; printed on Dec. 17, 2009.
"Nutritionmaker Focus Nutrition Software Motivate—Analyze—Instruct"; BioEX Systems, Inc.; bearing dates of 1995-2009; pp. 1-4; located at http://www.bioexsystems.com/NutritionMakerChiro.htm; printed on Dec. 17, 2009.
"Tired of a stiff neck and shoulders? Ergo Pro Computer Fatigue Software reminds you when to stretch and shows you how"; BioEX Systems, Inc.; bearing dates of 1995-2009; pp. 1-3; located at http://www.bioexsystems.com/ExerciseBreak.htm; printed on Dec. 17, 2009.
"VHI PC-Kits Desktop Edition"; Visual Health Information; pp.1-2; located at http://www.vhikits.com/products/software/PCKitsDesktop.aspx; printed on Dec. 17, 2009.
Wilson, Mark; "Philips DirectLife Turns Exercise Into a Status Bar"; Gizmodo; Bearing a date of Oct. 21, 2009; pp. 1-2; Creative Commons License; located at: http://gizmodo.com/5386577/philips-directlife-turns-exercise-into-a-status-bar; printed on Oct. 29, 2009.
"Free Exercise Programs—Workout Routines & Weight Loss Diet Plans"; Freetrainers.com; Bearing dates of 2000-2008; pp. 1-2; located at: http://www.freetrainers.com/FT/jsp/index.jsp; printed on Sep. 2, 2009.
"Your Personalized Development Plan"; Central Michigan University; Bearing a date of 2004; p. 1; located at: http://www.chsbs.cmich.edu/leader_model/dplanintro.htm; printed on Sep. 2, 2009.
Agger, Michael; "Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.
"Self-tracking links to get you started"; The Quantified Self: self knowledge through numbers; printed on Dec. 10, 2010; pp. 1-5; located at: http://quantifiedself.com/self-tracking-links-to-get-you-started/.
Gaonkar, Shravan, et al.; "Micro-Blog: Sharing and Querying Content Through Mobile Phones and Social Participation"; MobiSys '08; Jun. 17-20, 2008; pp. 174-186; ACM.

* cited by examiner

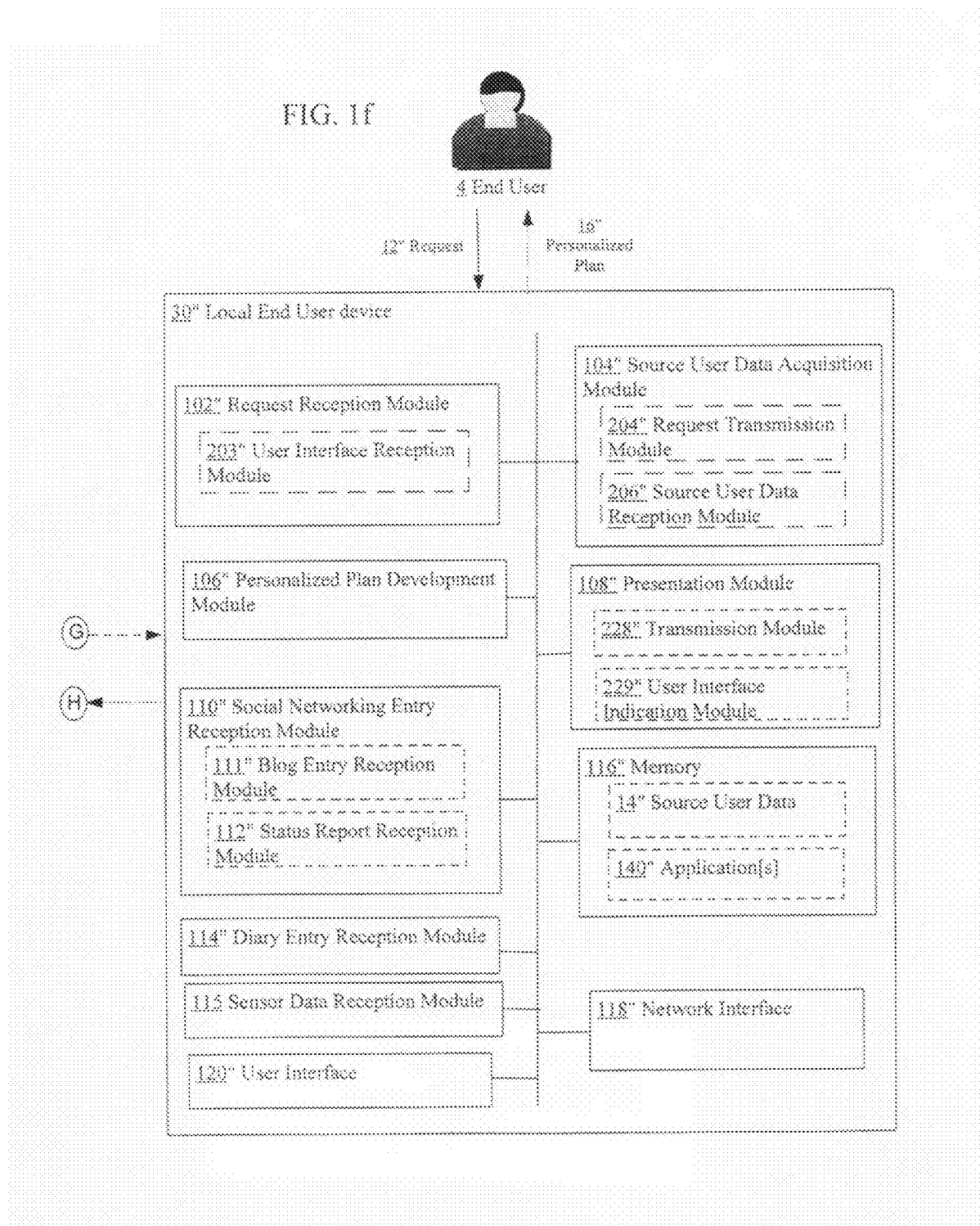

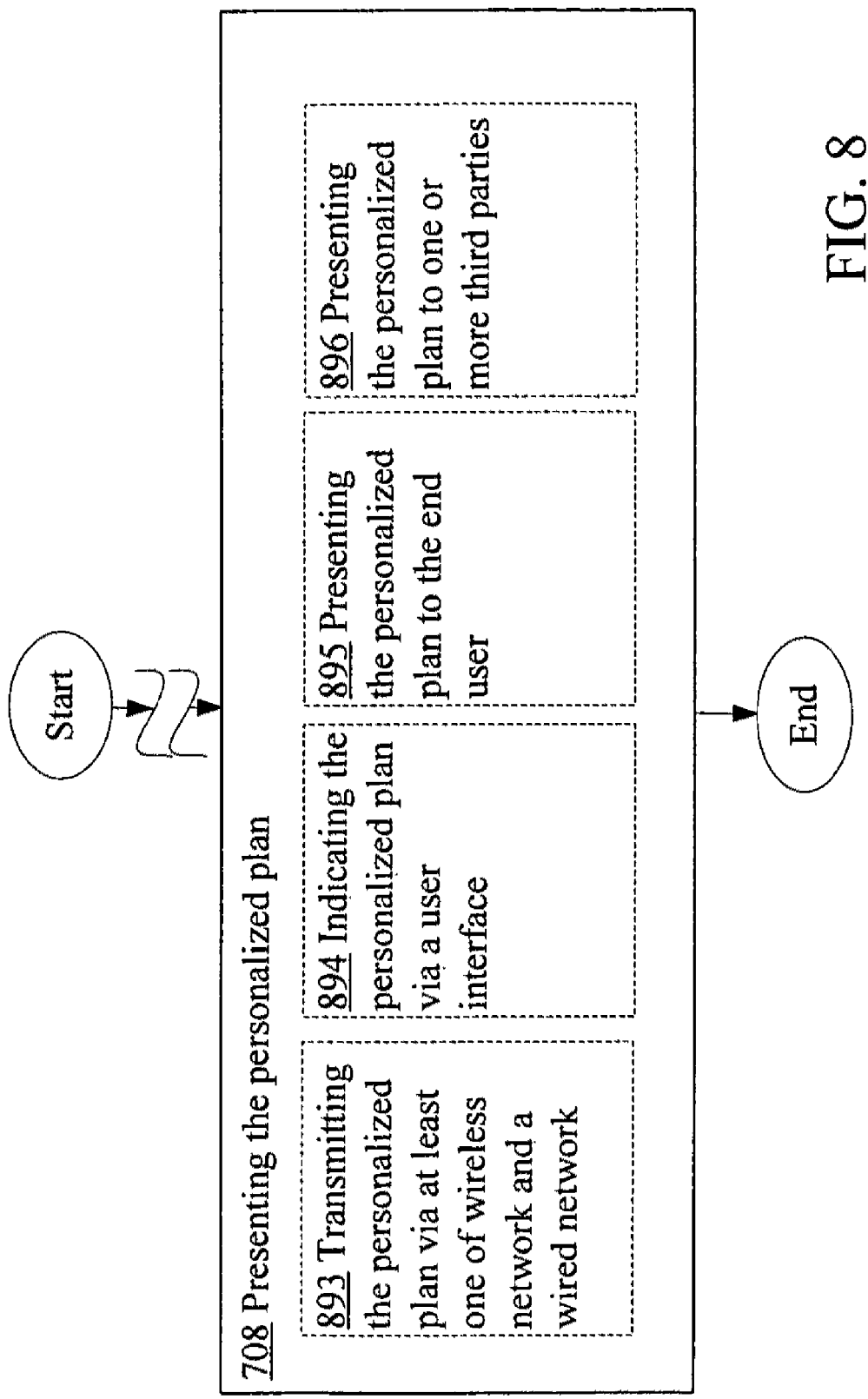

PERSONALIZED PLAN DEVELOPMENT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/584,489, entitled PERSONALIZED PLAN DEVELOPMENT, naming Shawn P. Firminger; Jason Garms; Roderick A. Hyde; Edward K.Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 3 Sep. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A computationally implemented method includes, but is not limited to receiving a request for a personalized plan designed to facilitate an end user to achieve one or more target outcomes when one or more emulatable aspects indicated by the personalized plan are emulated, the request identifying at least a source user; acquiring source user data indicating a plurality of reported aspects associated with at least the source user in response to receiving the request; and developing the personalized plan by at least determining which of the plurality of reported aspects associated with the source user are relevant to the achievement of the one or more target outcomes. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for receiving a request for a personalized plan designed to facilitate an end user to achieve one or more target outcomes when one or more emulatable aspects indicated by the personalized plan are emulated, the request identifying at least a source user; means for acquiring source user data indicating a plurality of reported aspects associated with at least the source user in response to receiving the request; and means for developing the personalized plan by at least determining which of the plurality of reported aspects associated with the source user are relevant to the achievement of the one or more target outcomes. In addition to the foregoing, other system aspects are described in the claims, drawings, and text forming a part of the present disclosure.

A computationally implemented system includes, but is not limited to: circuitry for receiving a request for a personalized plan designed to facilitate an end user to achieve one or more target outcomes when one or more emulatable aspects indicated by the personalized plan are emulated, the request identifying at least a source user; circuitry for acquiring source user data indicating a plurality of reported aspects associated with at least the source user in response to receiving the request and circuitry for developing the personalized plan by at least determining which of the plurality of reported aspects associated with the source user are relevant to the achievement of the one or more target outcomes. In addition to the foregoing, other system aspects are described in the claims, drawings, and text forming a part of the present disclosure.

A computer program product including a signal-bearing medium bearing one or more instructions for receiving a request for a personalized plan designed to facilitate an end user to achieve one or more target outcomes when one or more emulatable aspects indicated by the personalized plan are emulated, the request identifying at least a source user; one or more instructions for acquiring source user data indicating a plurality of reported aspects associated with at least the source user in response to receiving the request; and one or more instructions for developing the personalized plan by at least determining which of the plurality of reported aspects associated with the source user are relevant to the achievement of the one or more target outcomes. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 1e and 1f show a high-level block diagram of a local end user device 30" operating in a network environment.

FIG. 8 is a high-level logic flowchart of a process depicting alternate implementations of the presentation operation 708 of FIG. 7.

DETAILED DESCRIPTION

Figure 1A:
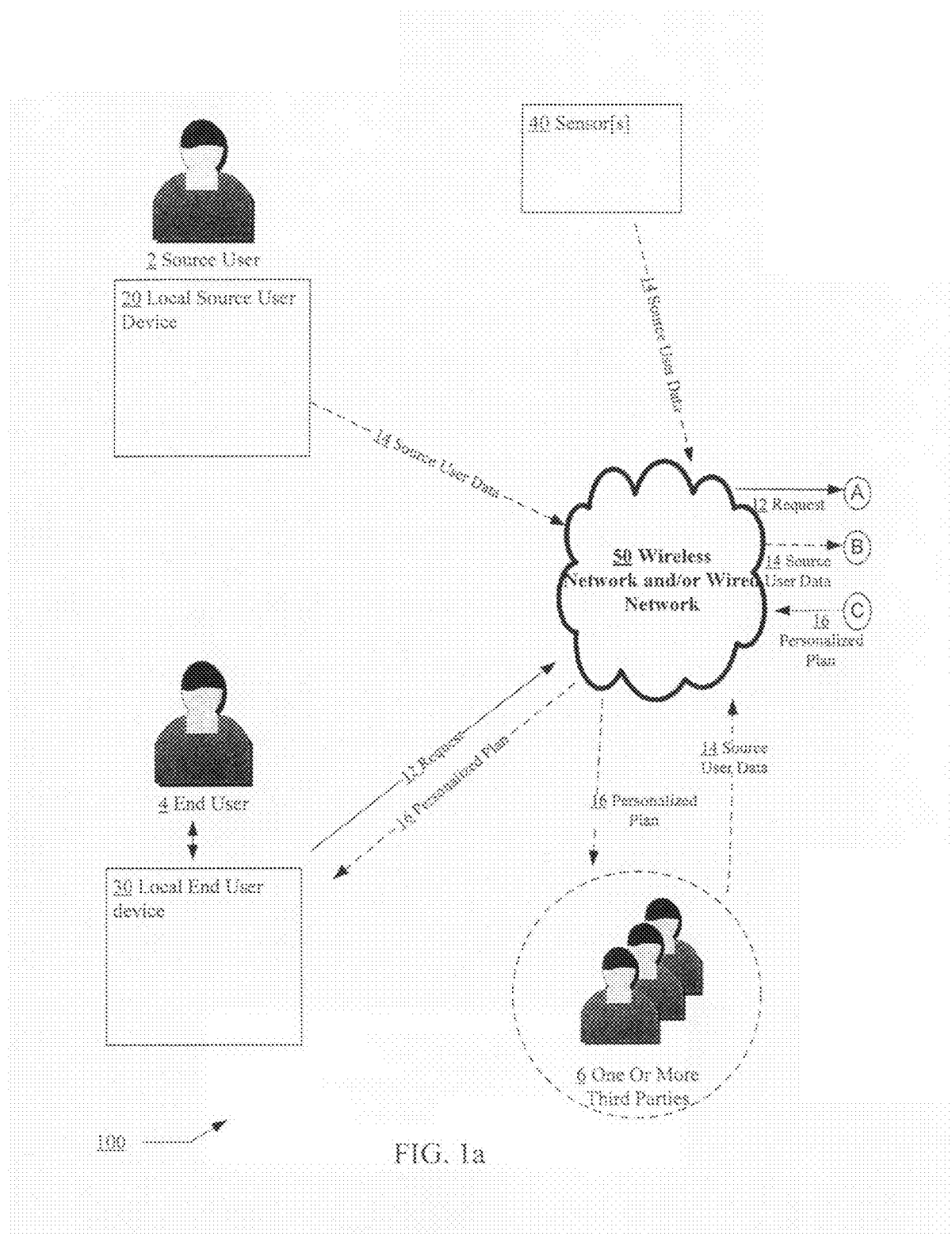
FIGS. 1*a* and 1*b* show a high-level block diagram of a server 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that has enjoyed explosive popularity in the computing/communication field is to electronically record one's daily activities, behaviors, thoughts, beliefs, traits, physical or mental states, physical characteristics, and other aspects of the person's everyday life onto an open diary. One place where such open diaries are maintained is at social networking sites commonly known as "blogs" where one or more users may report or post every aspect of their lives. The process of reporting or posting blog entries is commonly referred to as blogging. Newer types of blogs that are also becoming increasingly popular are known as microblogging or "twittering," whereby each of the microblogs that are posted are typically relatively short posts or entries, usually not more than 140 characters long.

Other social networking sites may allow users to update their personal information via, for example, social networking status reports in which a user may report or post for others to view the latest status or other aspects of the user. Although a wealth of personal information in the form of, for example, log data are now available through such social networking sites, it is only recently has there been any effort to exploit such useful data.

In particular embodiments, robust methods, systems, circuitry, and computer program products are provided that may facilitate in the development of a plan that when executed by, for example, an end user may result in the achievement of one or more target outcomes. In order to develop the plan, a model (e.g., a source user), who may be associated with the one or more outcomes, may be initially identified. The plan may then be developed by at least determining from a plurality of reported events or aspects associated with the model those reported aspects that may be relevant to the achievement of the one or more target outcomes. In some cases, the plurality of reported aspects may be indicated by, for example, log data such as data that may have been at least originally acquired through social networking entries (e.g., microblog entries and/or status reports), diary entries, and/or sensor readings.

More generally, and in accordance with various embodiments, the robust methods, systems, circuitry, and computer program products may facilitate in the development of a personalized plan designed to assist an end user in achieving one or more target outcomes when one or more emulatable aspects indicated by the personalized plan are emulated. In some implementations, a personalized plan may merely indicate a collection of one or more "emulatable aspects." An emulatable aspect may be any behavior, act, trait, physical state, mental state, social state, declaration, belief, or any other facet that may be emulated in order to achieve one or more target outcomes. In cases where the personalized plan includes multiple emulatable aspects, the personalized plan may or may not define a relationship or relationships (e.g., temporal, specific time, or spatial relationships) between the emulatable aspects.

A target outcome may be any type of goal or desired result that may be sought by an end user or by a third party. Examples of target outcomes include, for example, health-related outcomes such as weight loss or improved cardiovascular conditioning, athletic outcomes such as developing a particular athletic skill including being able to pitch a curve ball or achieving a particular golf handicap, physiological outcomes such as reduced blood pressure or blood glucose levels, social outcomes such as obtaining membership into an elite social club or attaining a particular social status, mental state outcomes such as achieving certain level of calmness or happiness, interpersonal or relational outcomes such as having lots of friends or developing skill to make friends, employment outcomes such as being promoted or developing certain work skills, and so forth.

In various implementations, the robust methods, systems, circuitry, and computer program products may begin developing the personalized plan when a request for the personalized plan designed to achieve the one or more target outcomes is initially received. Such a request may at least identify a source user who may be the model for achieving the one or more target outcomes. In other words, the source user may at least be perceived by, for example, an end user as having achieved the at least one or more target outcomes. In some cases, the source user may be an actual or "real" person. While in other cases, the source user may be a "fictional" person (e.g., an alter ego created by someone's imagination) that is associated with the one or more target outcomes. In still other cases, a source user may be a composite person created from data provided by a plurality of "real" persons.

In some cases where the source user is an actual or "real" person, the end user may have become aware of the source user when the end user accidently or randomly encountered the source user at some locale such as the gym, at school, at the doctor's office, on the street, or at some other locale. Upon encountering the source user, the end user may perceive that the source user is associated with some admirable quality (e.g., target outcome) and would like to have such a quality. For these cases, the end user may obtain the identity of the source user by a variety of alternative means. For instance, in situations where the end user randomly encounters the source user, the identity of the source user may be obtained by using some sort of sensing device that may be employed to unobtrusively acquire the identity of the source user. Example of such devices include, for example, a radio frequency identification (RFID) reader device (e.g., source user may carry an RFID), a facial recognition device, a device that determine the geographical location of a source user such as certain types of cellular telephones, and so forth.

Alternatively, a source user (e.g., actual, composite, or fictional person) may be listed at a website such as a social networking site. Such a website may allow an end user to access the identity of the source user as well as provide indications of one or more desirable qualities (e.g., target outcomes) associated with the source user.

In any event, in response to receiving the request for the personalized plan, "source user data" indicating one or more reported aspects associated with source user may be acquired (e.g., retrieved). In some implementations, the acquired source user data may be in the form of log data associated with the source user that may have been originally been obtained via social networking entries such as microblog entries or status reports, via diary entries, and/or via data entries provided by one or more sensors. Alternatively, such source user data may at least be partially fictional or fabricated.

After acquiring the source user data, the methods, systems, circuitry, and computer program products may develop the personalized plan by at least determining which of the one or more reported aspects associated with the source user and indicated by the source user data may be relevant to the achievement of the one or more target outcomes. After determining those reported aspects that are relevant to the achievement of the one or more target outcomes, the personalized plan may be developed by including into the personalized plan one or more emulatable aspects that corresponds to one or more identified reported aspects that are relevant to the achievement of the one or more target outcomes. In certain implementations, where the personalized plan includes a plurality of emulatable aspects, the personalized plan may define the relationships (e.g., temporal, specific time, and/or spatial relationships) between the emulatable aspects.

Figure 1B:
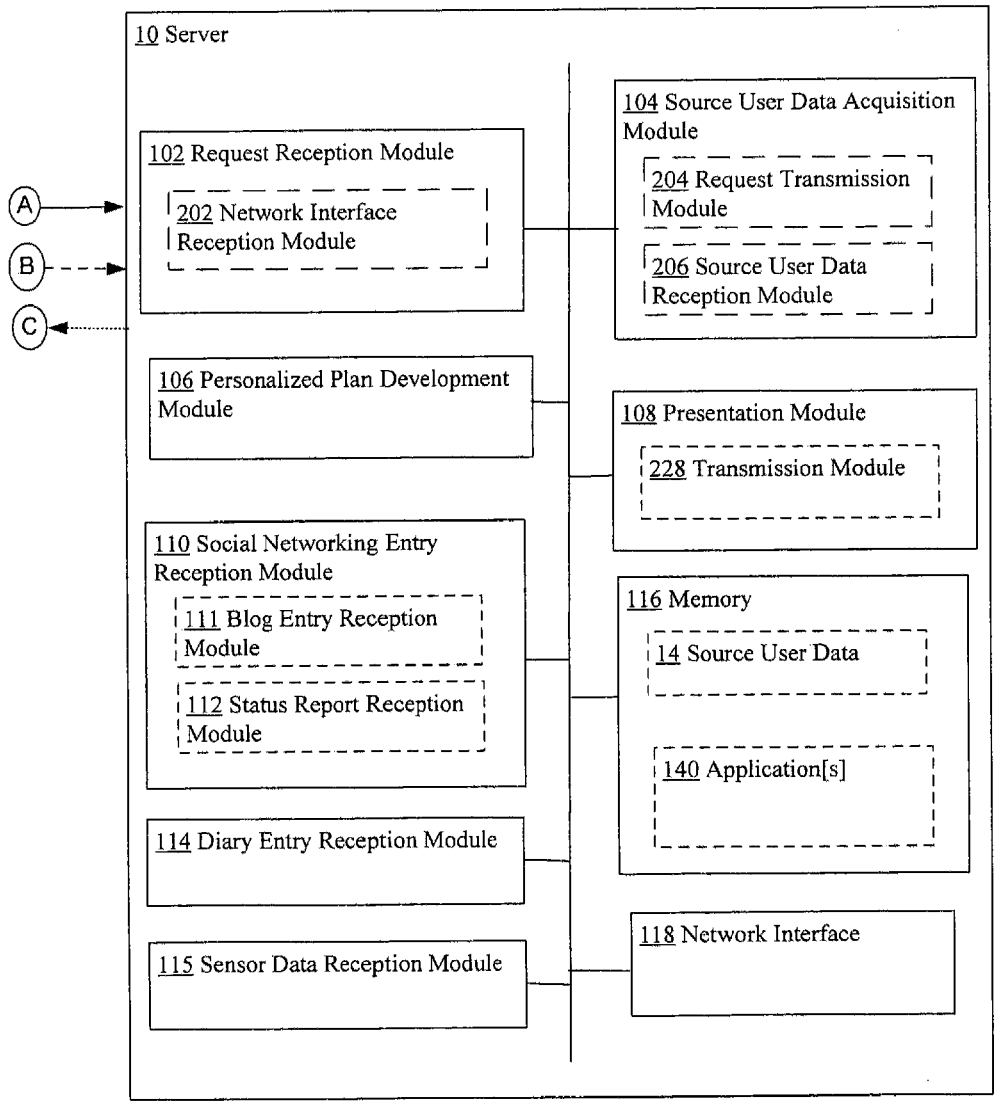
Figure 1C:
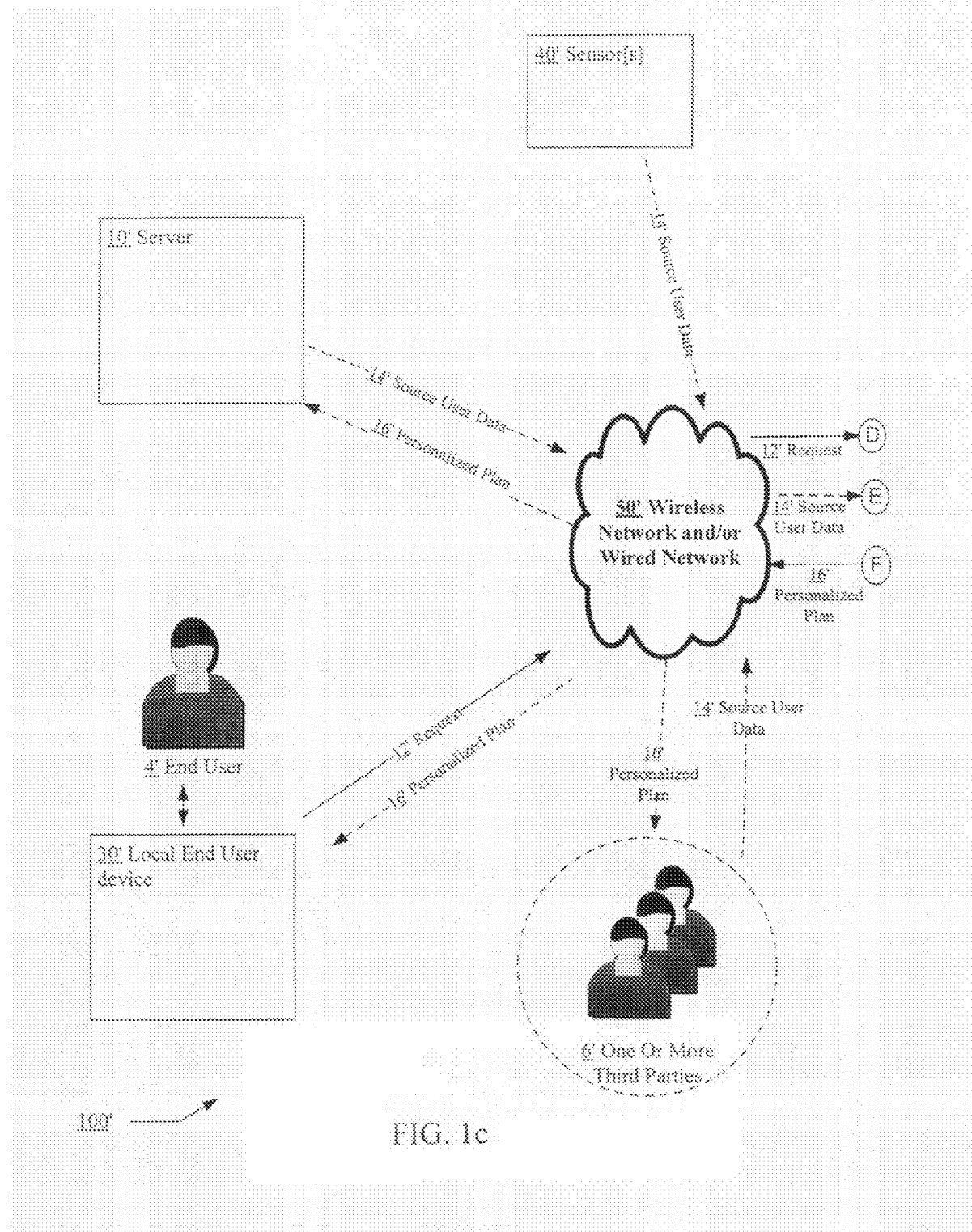
FIGS. 1c and 1d show a high-level block diagram of a local source user device 20' operating in a network environment.
Figure 1D:
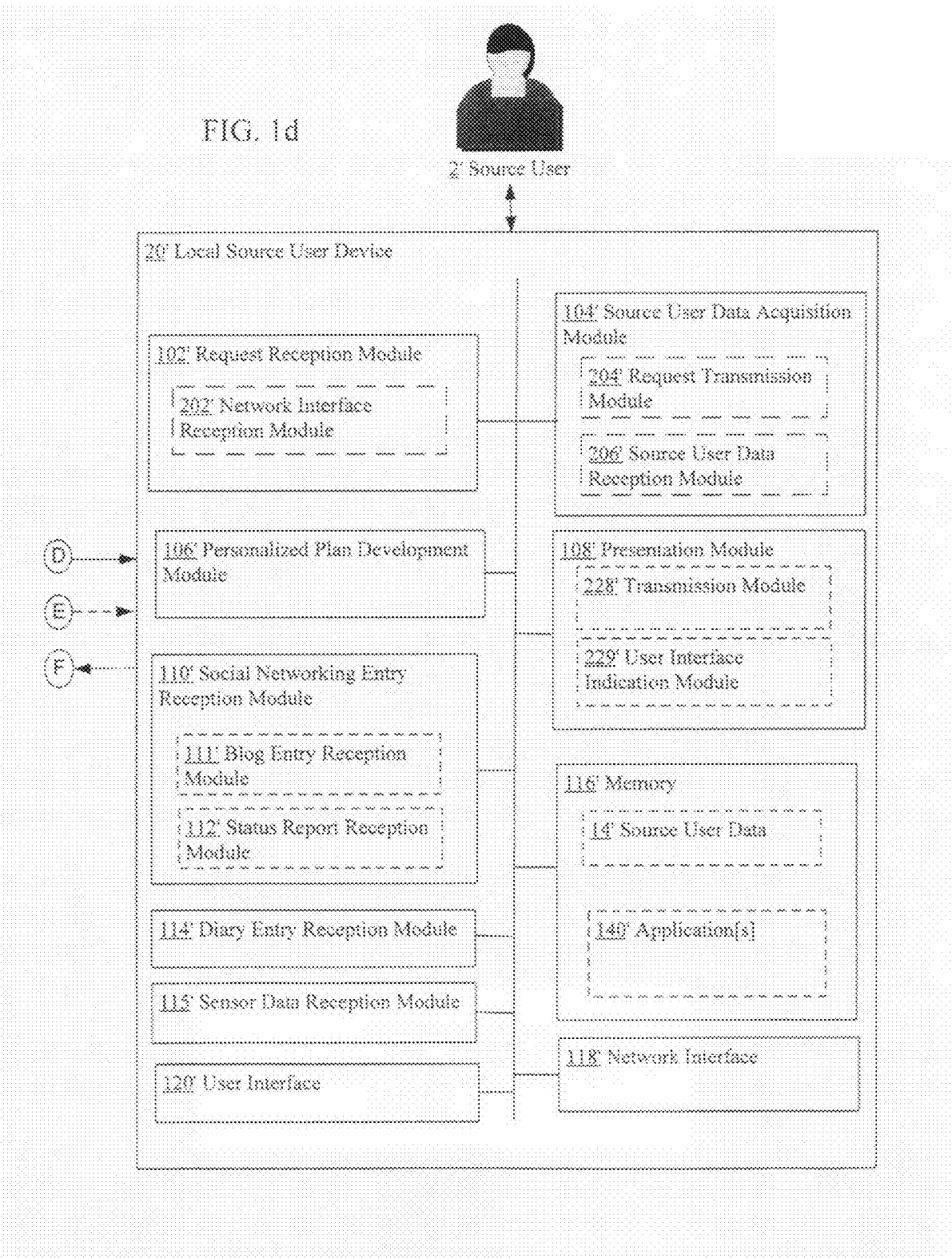
Figure 1E:
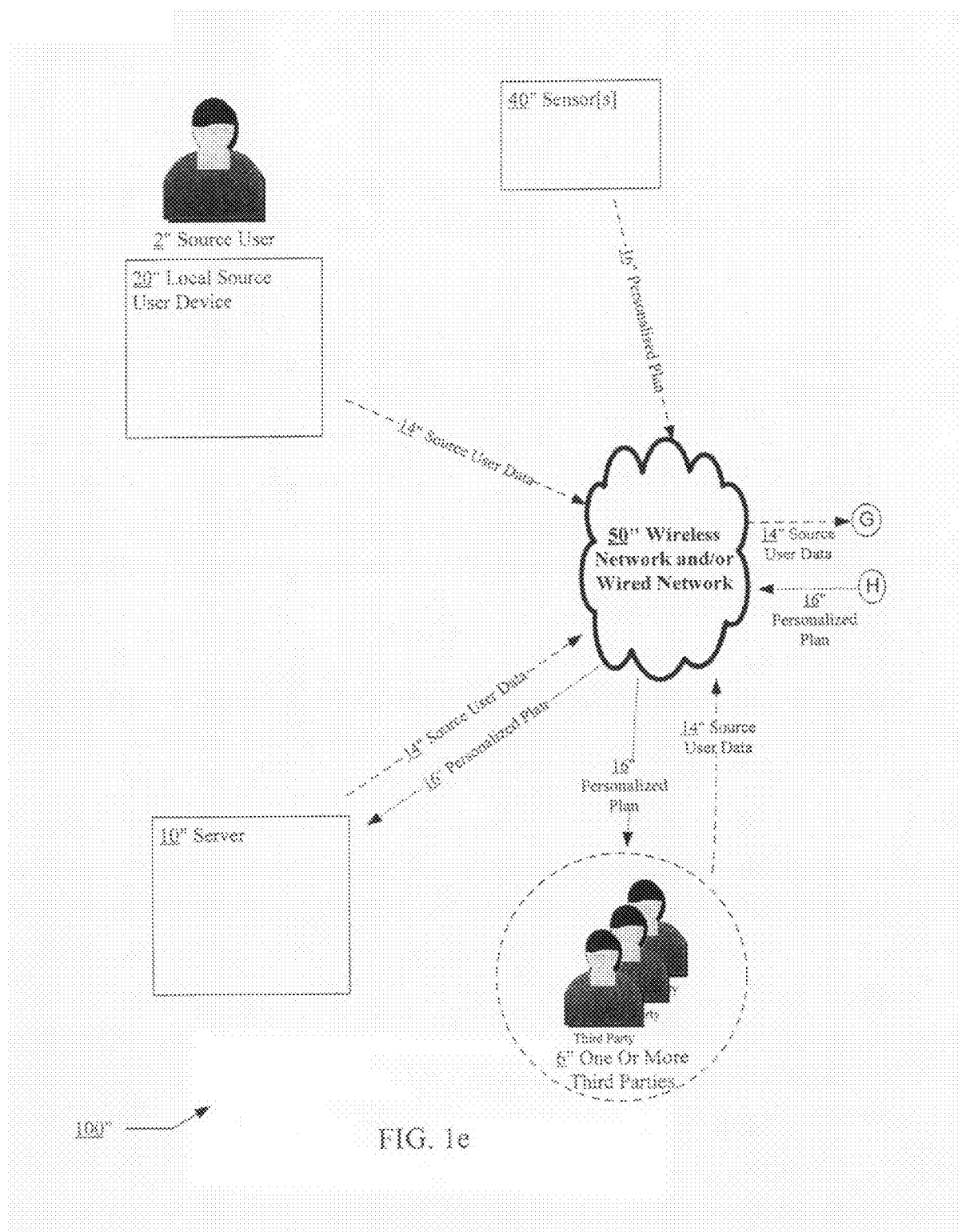

Turning now to FIGS. 1*a*, 1*b*, 1*c*, 1*d*, 1*e*, and 1*f*, illustrating three example environments in which the methods, systems, circuitry, and computer program products in accordance with various embodiments may be implemented by a computing device such as a server or a local user device. In particular, FIGS. 1*a* and 1*b* illustrates a first example environment in which the methods, systems, circuitry, and computer program products in accordance with some embodiments may be implemented at a server 10. FIGS. 1*c* and 1*d* illustrates a second example environment in which the methods, systems, circuitry, and computer program products in accordance with some embodiments may be implemented at a local source user device 20'. FIGS. 1*e* and 1*f* illustrate a third example environment in which the methods, systems, circuitry, and computer program products in accordance with some embodiments may be implemented at a local end user device 30". Note that in the following, "*" represents a wildcard. Thus, "server 10\*" in the following description may be in reference to server 10 of the first example environment of FIGS. 1*a* and 1*b*, to server 10' of the second example environment of FIGS. 1*c* and 1*d*, or to server 10" of the third example environment of FIGS. 1*e* and 1*f*.

In various embodiments, the server 10 of FIG. 1*b*, the local source user device 20' of FIG. 1*d*, and the local end user device 30" of FIG. 1*f* may be designed to, among other things, receive a request 12\* for a personalized plan 16\* that is designed to facilitate an end user 4\* to achieve one or more target outcomes when one or more emulatable aspects indicated by the personalized plan 16\* are emulated, the request 12\* identifying at least a source user 2\*. In response to the receiving the request 12\*, the server 10, the local source user device 20', and the local end user device 30" may be designed to acquire source user data 14\* that may indicate a plurality of reported aspects associated with the source user 2\*.

After acquiring the source user data 14\*, the server 10, the local source user device 20', and the local end user device 30" may be designed to develop the personalized plan 16\* by at least determining which of the plurality of reported aspects associated with the source user 2\* are relevant to the achievement of the one or more target outcomes. In some implementations, the server 10, the local source user device 20', and the local end user device 30" may be further designed to present the resulting personalized plan 16\*.

Referring particularly now to FIGS. 1*a* and 1*b* illustrated the first example environment in accordance with various embodiments. Included in the illustrated first environment of FIGS. 1*a* and 1*b* is a first exemplary system 100, which includes at least a server 10 (see FIG. 1*b*) that may be designed to communicate with at least a source user 2 (via a local source user device 20) and an end user 4 (via a local end user device 30) through a wireless network and/or wired network 50. In some implementations, the server 10 may further communicate with, via the wireless network and/or wired network 50, one or more third parties 6 such as one or more other source users, one or more other end users, one or more content providers, one or more network service providers, and/or one or more other third parties. The server 10 may also communicate with, via the wireless network and/or wired network 50, one or more sensors 40.

In various implementations, the server 10 of FIG. 1*b* (as well as the server 10' of FIG. 1*c* and the server 10" of FIG. 1*e*) may be a network server that is designed to interface with a wireless network and/or wired network 50\*. A network server, as will be described herein, may be in reference to a server located at a single network site or located across multiple network sites or a conglomeration of servers located at multiple network sites.

The local source user device 20 (as well as the local source user device 20' of FIG. 1d and the local source user device 20" of FIG. 1e) and the local end user device 30 (as well as the local end user device 30' of FIG. 1c and the local end user device 30" of FIG. 1f) may be a variety of computing/computing devices including, for example, a cellular phone, a personal digital assistant (PDA), a laptop, a desktop, or other types of computing/communication devices that can communicate with the computing device 10. In some embodiments, the local source user device 20 (as well as the local source user device 20' of FIG. 1d and the local source user device 20" of FIG. 1e) and/or the local end user device 30 (as well as the local end user device 30' of FIG. 1c and the local end user device 30" of FIG. 1f) may be a handheld device such as a cellular telephone, a smartphone, a Mobile Internet Device (MID), an Ultra Mobile Personal Computer (UMPC), a convergent device such as a personal digital assistant (PDA), and so forth.

In various embodiments, the one or more sensors 40 (as well as the one or more sensors 40' of FIG. 1c and the one or more sensors 40" of FIG. 1e) a wide range of devices that can monitor various aspects or events associated with a source user 2*. For example, in some implementations, the one or more sensors 40* may include devices that can monitor a user's physiological characteristics such as blood pressure sensors, heart rate monitors, glucometers, and so forth. In some implementations, the one or more sensors 40* may include devices that can monitor activities of a user (e.g., source user 2*) such as a pedometer, a toilet monitoring system (e.g., to monitor bowel movements), exercise machine sensors, an accelerometer to measure a person's movements which may indicate specific activities, and so forth. The one or more sensors 40* may also include other types of sensor/monitoring devices such as video or digital camera, global positioning system (GPS) to provide data that may be related to a user (e.g., locations of the source user 2*), and so forth.

Referring back to the first exemplary environment of FIGS. 1a and 1b, the server 10 may receive a request 12 for a personalized plan 16 from the end user 4 via the local end user device 30. The request 12 may identify at least a source user 2. The requested personalized plan 16 may be designed to facilitate the end user 4 to achieve one or more target outcomes when one or more emulatable aspects indicated by the personalized plan 16 are emulated. In response to receiving the request 12, the server 10 may acquire source user data 14 that may indicate a plurality of reported aspects associated with at least the source user 2. The source user data 14 may be acquired from a variety of sources. For example, in some implementations, at least a portion of the source user data 14 may be acquired from a memory 116. In some implementations, at least a portion of the source user data 14 may be acquired from the local source user device 20. In some implementations, at least a portion of the source user data 14 may be acquired from the one or more third parties. In some implementations, at least a portion of the source user data 14 may be acquired from one or more sensors 40.

After acquiring the source user data 14, the server 10 may develop the personalized plan 16 by at least determining which of the plurality of reported aspects associated with the source user 2 are relevant to the achievement of the one or more target outcomes. In some implementations, the server 10 may then present the developed personalized plan 16 to the end user 4 (via the local end user device 30) and/or to one or more third parties 6.

The server 10 as illustrated in FIG. 1b may include a variety of modules, sub-modules, and components. As shown, the server 10 may include a request reception module 102 (which may further include a network interface reception module 202, a source user data acquisition module 104 (which may further include a request transmission module 204 and/or source user data reception module 206), a personalized plan development module 106, a presentation module 108 (which may further include a transmission module 228), a memory 116 (which may store source user data 14 and/or one or more applications 140), and/or a network interface 118 (e.g., a network interface card or NIC). The server 10, in various implementations, may further include a social networking entry reception module 110 (which may further include a blog entry reception module 111 and/or status report reception module 112), a diary entry reception module 114, and/or a sensor data reception module 115.

The request reception module 102 may be configured to, among other things, receive a request 12 for a personalized plan 16 that is designed to facilitate an end user 4 to achieve one or more target outcomes when one or more emulatable aspects indicated by the personalized plan 16 are emulated. The request 12 to be received by the request reception module 102 may at least identify a source user 2. In some implementations, the request 12 to be received by the request reception module 102 may further include information that may facilitate in the development of the personalized plan 16 as will be further described herein. In order to facilitate reception of a request 12 from, for example, a network device (e.g., local end user device 30 or another server), the request reception module 102 may include a network interface reception module 202 designed to receive the request 12 via a wireless network and/or wired network 50.

The source user data acquisition module 104 may be configured to acquire, in response to the request reception module 102 receiving the request 12, source user data 14 indicating a plurality of reported aspects associated with at least the source user 2. In various implementations, the source user data acquisition module 104 may further include a request transmission module 204 designed to transmit (e.g., via the wireless network and/or wired network 50) a request for the source user data 14, and a source user data reception module 206 designed to receive the source user data 14. The source user data 14 acquired by the source user data acquisition module 104 may indicate, in various implementations, at least a first one or more reported aspects that may be relevant to the achievement of the one or more target outcomes of the personalized plan 16, and a second one or more reported aspects that may not be relevant to the achievement of the one or more target outcomes.

Figure 2:
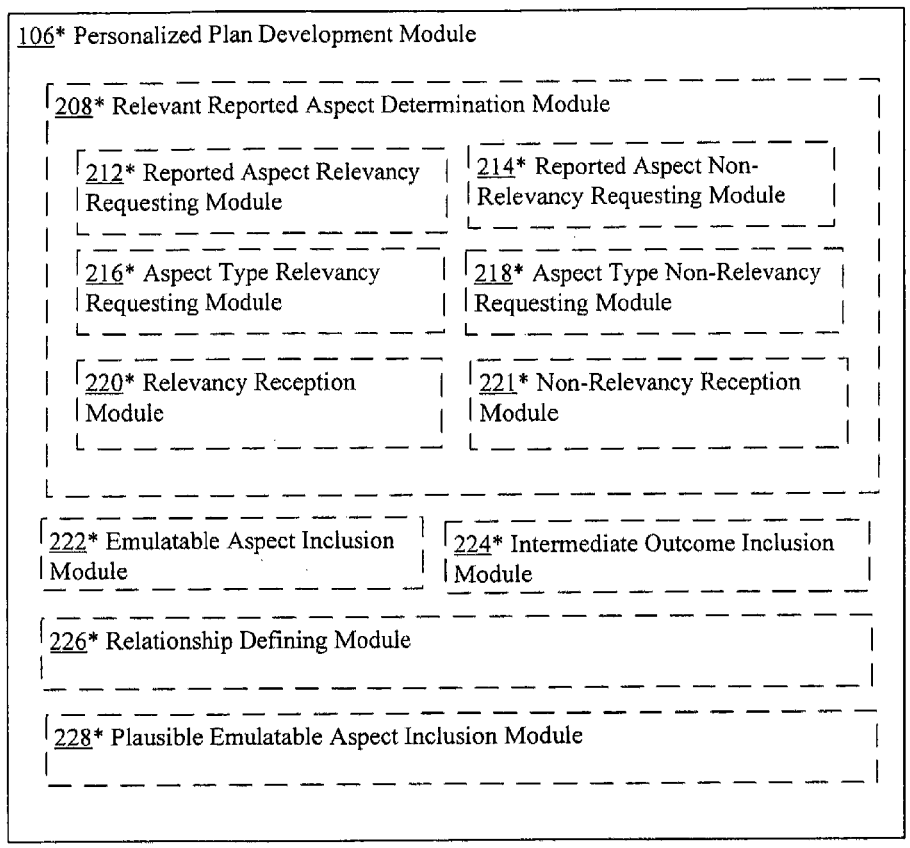
FIG. 2 shows another perspective of the personalized plan development module 106* of the server 10 of FIG. 1b, of the local source user device 20' of FIG. 1d, and of the local end user device 30" of FIG. 1f.

The personalized plan development module 106 may be configured to, among other things, develop a personalized plan 16 by at least determining which of the plurality of reported aspects associated with the source user 2 as indicated by the source user data 14 are relevant to the achievement of the one or more target outcomes of the personalized plan 16. For example, filtering the source user data 14 to determine or distinguish those reported aspects (e.g., first one or more reported aspects) that are relevant to the achievement of the one or more target outcomes from those reported aspects (e.g., second one or more reported aspects) that are not relevant to the achievement of the one or more target outcomes. After determining which of the reported aspects associated with the source user 2 are relevant to the achievement of the one or more target outcomes, the personalized plan development module 106 may develop the personalized plan 16 by including into the personalized plan 16 one or more emulatable aspects that corresponds to one or more reported aspects that have been determined to be relevant to the achievement of the one or more target outcomes. As will be further described herein, the personalized plan development module 106 in various implementations may further include one or more sub-modules as will be further described herein and as illustrated in FIG. 2.

The presentation module 108 may be configured to present the personalized plan 16 developed by the personalized plan development module 106 to the end user 4, the source user 2, and/or one or more third parties 6. In some implementations, presentation module 108 may further include a transmission module 228 that is configured to transmit the personalized plan 16 via, for example, the wireless network and/or wired network 50.

A more detailed discussion relating to the request reception module 102, the source user data acquisition module 104, the personalized plan development module 106, the presentation module 108, and their sub-modules, will be provided below with respect to the various operational flows to be described herein. The social networking entry reception module 110 may be configured to receive social networking entries from various sources including, for example, the source user 2, the end user 4, and/or one or more third parties 6. The social networking entry reception module 110 may further include a blog entry reception module 111 that is configured to receive blog or microblog entries and/or a status report reception module 112 configured to receive status reports. Similarly, the diary entry reception module 114 may be configured to receive diary entries from, for example, the source user 2, the end user 4, and/or from one or more third parties 6.

The sensor data reception module 115 may be configured to receive sensing data from one or more sensors 40. The memory 116 may comprise one or more volatile and/or nonvolatile devices that may be used to store data. In various implementations, the memory 116 may include, for example, a mass storage device, read-only memory (ROM), programmable read-only memory (PROM), erasable programmable read-only memory (EPROM), cache memory such as random access memory (RAM), flash memory, synchronous random access memory (SRAM), dynamic random access memory (DRAM), and/or other memory devices. The one or more applications 140 that may be included in the memory 116 may comprise of, for example, one or more communication applications (e.g., text messaging application, instant messaging application, email application, voice recognition system, and so forth), Web 1.0 application, and/or Web 2.0 application to facilitate in communicating via, for example, the World Wide Web.

Referring now to FIGS. 1c and 1d, which as previously indicated, illustrates a second example environment in which the methods, systems, circuitry, and computer program products in accordance with various embodiments may be implemented at a local source user device 20' rather than at a server 10' as was the case in the first example environment of FIGS. 1a and 1b. As illustrated, the second example environment of FIGS. 1c and 1d is similar to the first example environment of FIGS. 1a and 1b.

In general, the second example environment of FIGS. 1c and 1d may include a second exemplary system 100', which includes at least a local source user device 20' (see FIG. 1d). In various implementations, the local source user device 20' as was the case for server 10 of FIGS. 1a and 1b may be designed to receive a request 12' for a personalized plan 16' designed to facilitate an end user 4' to achieve one or more target outcomes via a wireless network and/or wired network 50'. In some implementations, the request 12' may be received from an end user 4'. Alternatively, and although not depicted, the request 12' may be received from a server 10' or from one or more third parties 6'. Note that server 10 of the first example environment of FIGS. 1a and 1b may also receive the request 12 from other sources (e.g., another server or one or more third parties 6) other than from an end user 4.

In any event, in response to receiving the request 12', the local source user device 20' may be designed to acquire source user data 14' indicating a plurality of reported aspects associated with a source user 2' from one or more sources including, for example, a memory 116', a server 10', one or more sensors 40', and/or one or more third parties 6'. The source user data 14' acquired by the local source user device 20' may indicate, in various implementations, at least a first one or more reported aspects that may be relevant to the achievement of the one or more target outcomes of the personalized plan 16', and a second one or more reported aspects that may not be relevant to the achievement of the one or more target outcomes. The local source user device 20' may be further designed to develop a personalized plan 16' by at least determining which of the reported aspects associated with the source user 2' may be relevant to the achievement of the one or more target outcomes. For example, the local source user device 20' may be designed to filter the source user data 14' to determine or distinguish those reported aspects (e.g., first one or more reported aspects) that are relevant to the achievement of the one or more target outcomes from those reported aspects (e.g., second one or more reported aspects) that are not relevant to the achievement of the one or more target outcomes. In some implementations, the local source user device 20' may be further designed to present the developed personalized plan 16' to the end user 4', one or more third parties 6', and/or a server 10'.

The local source user device 20', as illustrated in FIG. 1d, may include the same or similar modules, sub-modules, and components included in the server 10 of FIG. 1b. As illustrated, the local source user device 20' may include a request reception module 102' (which may further include a network interface reception module 202', a source user data acquisition module 104' (which may further include a request transmission module 204' and a source user data reception module 206'), a personalized plan development module 106', a presentation module 108' (which may further include a transmission module 228'), a memory 116' (which may store source user data 14' and/or one or more applications 140'), and/or a network interface 118', similar to the server 10 of FIG. 1b.

Also similar to server 10 of FIG. 1b, the local source user device 20' may also include a social networking entry reception module 110' (which may further include a blog entry reception module 111' and/or a status report reception module 112'), a diary entry reception module 114', and/or a sensor data reception module 115'. All of these modules, sub-modules, and components of the local source user device 20' may perform the same or similar functions as their counterparts that may be included in the server 10 of FIG. 1b. In addition to these modules, sub-modules, and components, the local source user device 20' may include a user interface 120' and a user interface indication module 229' (which may be included with the presentation module 108'). The user interface indication module 229' may be designed to indicate, for example, the personalized plan 16' via the user interface 120'. The user interface 120' may include one or more of, for example, a display monitor, a touchscreen, a keyboard, a keypad, a mouse, an audio system including one or more speakers, a microphone, an image capturing device such as a digital camera, and so forth.

Turning now to FIGS. 1e and 1f, which as previously indicated, illustrates a third example environment in which the methods, systems, circuitry, and computer program products in accordance with various embodiments may be implemented at a local end user device 30" rather than at a server 10" or at a local source user device 20" as was the case in the first and second example environments of FIGS. 1a and 1b and FIGS. 1c and 1d. The third example environment of FIGS. 1e and 1f is similar to the first example environment of FIGS. 1a and 1b and the second example environment of FIGS. 1c and 1d with few minor differences. For example, in the third example environment, the local end user device 30" may receive a request 12" for a personalized plan 16" directly from an end user 4* via a user interface 120" rather than from the wireless network and/or wired network 50" as was the case for the server 10 of the first example environment of FIGS. 1a and 1b and as was the case for the local source user device 20' of the second example environment of FIGS. 1c and 1d. However, and as with the server 10 and the local source user device 20' of FIGS. 1b and 1d, the local end user device 30" may also alternatively receive a request 12" via the wireless network and/or wired network 50" from other sources such as from one or more third parties 6" or from a server 10".

As illustrated, the third example environment of FIGS. 1e and 1f may include a third exemplary system 100", which includes at least a local end user device 30" (see FIG. 1f). In general, the local end user device 30" may be designed to receive a request 12" for a personalized plan 16" for facilitating an end user 4" in achieving one or more target outcomes. In some implementations, the request 12" may be received directly from the end user 4" via a user interface 120". Alternatively, and although not depicted, the request 12" may be received via wireless network and/or wired network 50" from, for example, one or more third parties 6" or from a server 10".

In response to receiving the request 12", the local end user device 30" may be designed to acquire source user data 14" indicating a plurality of reported aspects associated with a source user 2" from one or more sources including, for example, a memory 116", a server 10", one or more sensors 40", and/or one or more third parties 6". The source user data 14" acquired by the local end user device 30" may indicate, in various implementations, at least a first one or more reported aspects that may be relevant to the achievement of the one or more target outcomes of the personalized plan 16", and a second one or more reported aspects that may not be relevant to the achievement of the one or more target outcomes. The local end user device 30" may be further designed to develop a personalized plan 16" by at least determining which of the reported aspects associated with the source user 2" may be relevant to the achievement of the one or more target outcomes. For example, the local end user device 30" may be designed to filter the source user data 14" to determine or distinguish those reported aspects (e.g., first one or more reported aspects) that are relevant to the achievement of the one or more target outcomes from those reported aspects (e.g., second one or more reported aspects) that are not relevant to the achievement of the one or more target outcomes. In various implementations, the local end user device 30" may be further designed to present the developed personalized plan 16" to the end user 4" (e.g., via the user interface 120"), to one or more third parties 6" (e.g., via wireless network and/or wired network 50"), and/or to a server 10" (e.g., via wireless network and/or wired network 50").

In various implementations, the local end user device 30" may include the same or similar modules, sub-modules, and components included in the local source user device 20' of FIG. 1d. For example, the local end user device 30" may include a request reception module 102", a source user data acquisition module 104" (which may further include a request transmission module 204" and a source user data reception module 206"), a personalized plan development module 106", a presentation module 108" (which may further include a transmission module 228" and a user interface indication module 229"), a memory 116" (which may store source user data 14" and/or one or more applications 140"), a user interface 120", and/or a network interface 118", similar to the local source user device 20' of FIG. 1d. Also similar to the local source user device 20' of FIG. 1d, the local end user device 30" may also include a social networking entry reception module 110" (which may further include a blog entry reception module 111" and/or a status report reception module 112"), a diary entry reception module 114", and/or a sensor data reception module 115". All of these modules, sub-modules, and components of the local end user device 30" may perform the same or similar functions as their counterparts that may be included in the local source user device 20' of FIG. 1d. In addition to these modules, sub-modules, and components, the local end user device 30" may include a user interface reception module 203" (which may be included in the request reception module 102") for receiving the request 12" via a user interface 120". The user interface 120" may include one or more of, for example, a display monitor, a touchscreen, a keyboard, a keypad, a mouse, an audio system including one or more speakers, a microphone, an image capturing device such as a digital camera, and so forth.

FIG. 2 illustrates the personalized plan development module 106* (e.g., personalized plan development module 106, personalized plan development module 106', and personalized plan development module 106") of FIGS. 1b, 1d, and 1f. As illustrated, the personalized plan development module 106* may include a relevant reported aspect determination module 208* that is configured to, among other things, determine which of a plurality of reported aspects associated with a source user 2*, as indicated by source user data 14*, are relevant to the achievement of one or more target outcomes of a personalized plan 16*. In various implementations, the relevant reported aspect determination module 208* may be further configured to, among other things, determine which of the plurality of the reported aspects, as indicated by the source user data 14*, occurred within a predefined time period from occurrence of one or more reported outcomes associated with the source user 2* that corresponds to the one or more target outcomes of the personalized plan 16*. In the same or different implementations, the relevant reported aspect determination module 208* may be configured to determine which of the reported aspects as indicated by the source user data 14*are relevant to the achievement of the one or more target outcomes based, at least in part, on indications provided by the source user 2*, by the end user 4*, and/or by one or more third party sources.

The relevant reported aspect determination module 208* may further include one or more sub-modules in various alternative implementations. For example, in various implementations, the relevant reported aspect determination module 208* may include one or more of a reported aspect relevancy requesting module 212*, a reported aspect non-relevancy requesting module 214*, an aspect type relevancy requesting module 216*, an aspect type non-relevancy requesting module 218*, a relevancy reception module 220*, and/or a non-relevancy reception module 221*. In brief, the reported aspect relevancy requesting module 212* may be configured to, among other things, request the source user 2* or the end user 4* to provide one or more indications of which of the reported aspects (as indicated by the source user data 14*) are relevant to the achievement of one or more reported outcomes (as may be indicated by the source user data 14*) that corresponds to the one or more target outcomes of the personalized plan 16*.

In contrast, the reported aspect non-relevancy requesting module 214 may be configured to, among other things, request the source user 2* or the end user 4* to provide one or more indications of which of the reported aspects (as indicated by source user data 14*) are not relevant to the achievement of one or more reported outcomes (as may be indicated by the source user data 14*) that corresponds to the one or more target outcomes of the personalized plan 16*. The aspect type relevancy requesting module 216* may be configured to, among other things, request the end user 4* or the source user 2* to provide one or more indications of what types of aspects are relevant to the achievement of the one or more target outcomes of the personalized plan 16*. In contrast, the aspect type non-relevancy requesting module 218* may be configured to, among other things, request the end user 4* or the source user 2* to provide one or more indications of what types of aspects are relevant to the achievement of the one or more target outcomes of the personalized plan 16*.

The relevancy reception module 220* may be configured to receive (e.g., receive from a source user 2*, an end user 4*, or one or more third parties 6*) indications as to which reported aspects or which types of reported aspects are relevant to the achievement of the one or more target outcomes of the personalized plan 16*. In contrast, the non-relevancy reception module 221* may be configured to receive (e.g., receive from a source user 2*, an end user 4*, or one or more third parties 6*) indications as to which reported aspects or which types of reported aspects are not relevant to the achievement of the one or more target outcomes of the personalized plan 16*.

In various alternative implementations, the personalized plan development module 106* may further include one or more of an emulatable aspect inclusion module 222*, an intermediate outcome inclusion module 224*, a relationship defining module 226*, and/or a plausible emulatable aspect inclusion module 228*. The emulatable aspect inclusion module 222* may be configured to, among other things, facilitate the development of the personalized plan 16* by including into the personalized plan 16 at least one emulatable aspect that corresponds to at least one reported aspect associated with the source user 2* that is determined to be relevant to the achievement of the one or more target outcomes of the personalized plan 16*. The intermediate outcome inclusion module 224* may be configured to, among other things, facilitate the development of the personalized plan 16* by including into the personalized plan 16* at least one intermediate outcome that corresponds to one or more reported intermediate outcomes as indicated by the source user data 14*. The relationship defining module 226* may be configured to, among other things, facilitate the development of the personalized plan 16* by defining in the personalized plan 16* a relationship or relationships (e.g., temporal, specific time, or spatial relationships) between a plurality of emulatable aspects that may be included in the personalized plan 16*. The plausible emulatable aspect inclusion module 228 may be configured to, among other things, facilitate the development of the personalized plan 16* by including into the personalized plan 16* at least one plausible emulatable aspect, the at least one plausible emulatable aspect being at least one emulatable aspect that has been successfully emulated by one or more other end users (e.g., one or more third parties 6*).

A more detailed discussion related to the server 10 of FIG. 1b, the local source user device 20' of FIG. 1d, and the local end user device 30" of FIG. 1f will now be provided with respect to the processes and operations to be described herein.

Figure 3:
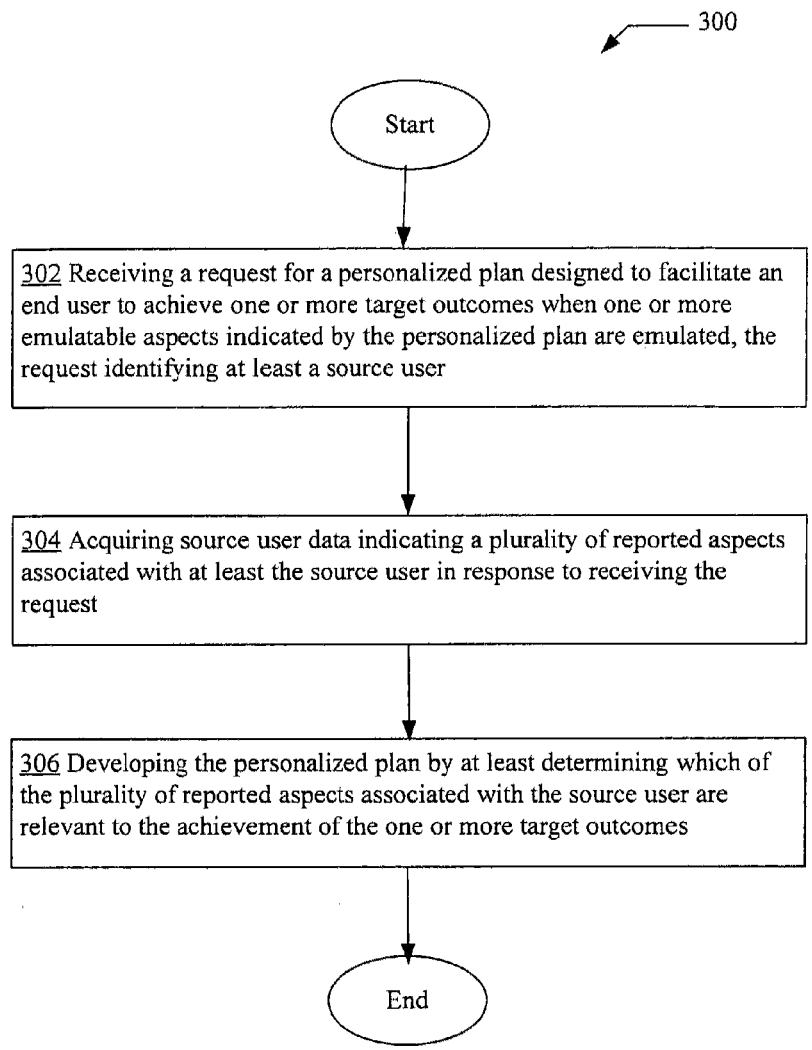
FIG. 3 is a high-level logic flowchart of a process.

FIG. 3 illustrates an operational flow 300 representing example operations related to, among other things, development of a personalized plan 16* designed to facilitate an end user 4* to achieve one or more target outcomes by at least determining which of a plurality of reported aspects associated with a source user 2* are relevant to the achievement of the one or more target outcomes. In some embodiments, the operational flow 300 may be executed by, for example, the server 10 of FIG. 1b, the local source user device 20' of FIG. 1d, or the local end user device 30" of FIG. 1f.

In FIG. 3 and in the following figures that include various examples of operational flows, discussions and explanations may be provided with respect to the three exemplary environments described above as illustrated in FIGS. 1a and 1b, FIGS. 1c and 1d, and FIGS. 1e and 1f, and/or with respect to other examples (e.g., as provided in FIG. 2) and contexts. However, it should be understood that the operational flows may be executed in a number of other environments and contexts, and/or in modified versions of FIGS. 1a to 1f, and 2. Also, although the various operational flows are presented in the sequence(s) illustrated, it should be understood that the various operations may be performed in other orders than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a reception operation 302 for receiving a request for a personalized plan designed to facilitate an end user to achieve one or more target outcomes when one or more emulatable aspects indicated by the personalized plan are emulated, the request identifying at least a source user. For instance, and as a illustration, the request reception module 102* (e.g., the request reception module 102, the request reception module 102', or the request reception module 102") of the server 10 of FIG. 1b, the local source user device 20' of FIG. 1d, or the local end user device 30" of FIG. 1f receiving a request 12* (e.g., via a wireless network and/or wired network 50* or via a user interface 120*) for a personalized plan 16* designed to facilitate an end user 4* to achieve one or more target outcomes (e.g., weight loss, development or improvement of user skills such as work skills, athletic or game skills, or social skills, developing or having particular subjective user states such as well-rested and/or well-being, and so forth) when one or more emulatable aspects (e.g., one or more behaviors, one or more acts, one or more beliefs, one or more traits, and/or other types of characteristics or traits) indicated by the personalized plan 16* are emulated, the request identifying at least a source user 2*. Note that in various implementations the request 12* does not need to specify the one or more target outcomes associated with the requested personalized plan 16*. Instead, the request 12* may merely identify a particular source user 2*. The identification of the source user 2* in the request 12* may be made by various means including, for example, by actual name (e.g., "John Doe"), by a user name (e.g., "jdoe"), by a facial image of the source user, by RFID identification, by voice identification, by location identification, by title identification, and so forth.

Operational flow 300 may also include an acquisition operation 304 for acquiring source user data indicating a plurality of reported aspects associated with at least the source user in response to receiving the request. For instance, and as a illustration, the source user data acquisition module 104* of the server 10 of FIG. 1b, of the local source user device 20' of FIG. 1d, or of the local end user device 30" of FIG. 1f acquiring (e.g., acquiring from a memory 116* and/or from a wireless network and/or wired network 50*) source user data 14* indicating a plurality of reported aspects (e.g., reported acts, behavior, beliefs, and so forth) associated with at least the source user 2* in response to receiving the request 12*.

Finally, operational flow 300 may include a development operation 306 for developing the personalized plan by at least determining which of the plurality of reported aspects associated with the source user are relevant to the achievement of the one or more target outcomes. For instance, and as a illustration, the personalized plan development module 106* including the relevant reported aspect determination module 208* of the server 10 of FIG. 1b, of the local source user device 20' of FIG. 1d, or of the local end user device 30" of FIG. 1f developing (e.g., creating) the personalized plan 16* by having the relevant reported aspect determination module 208* at least determining which of the plurality of reported aspects associated with the source user 2* are relevant to the achievement of the one or more target outcomes.

Figure 4A:
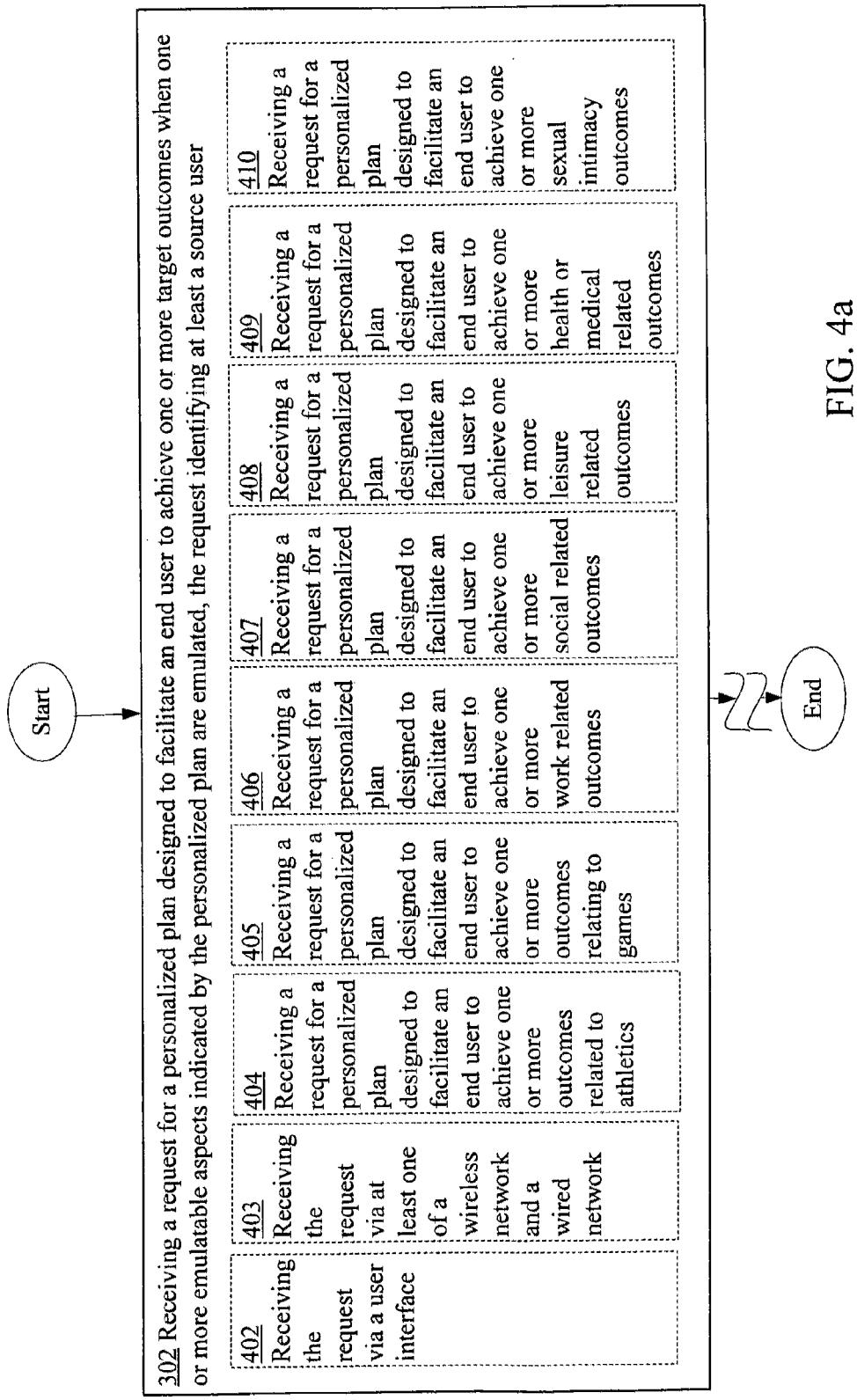
FIG. 4a is a high-level logic flowchart of a process depicting alternate implementations of the reception operation 302 of FIG. 3.

In various implementations, the reception operation 302 of FIG. 3 may be performed in various alternative ways as illustrated in FIGS. 4a, 4b, 4c, 4d, and 4e. For example, the request 12* received through the reception operation 302 may be received by various means depending upon, for example, whether the operation is being implemented at a server 10 (e.g., as in the embodiment depicted in FIGS. 1a and 1b), at a local source user device 20' (e.g., as in the embodiment depicted in FIGS. 1c and 1d), or at a local end user device 30" (e.g., as in the embodiment depicted in FIGS. 1e and 1f). For example, in some implementations the reception operation 302 may include an operation 402 for receiving the request via a user interface as depicted in FIG. 4a. For instance, the user interface reception module 203" of the local end user device 30" receiving the request 12" via a user interface 120" (e.g., an audio system including a microphone, a keypad, a touchscreen, a mouse, and so forth).

In some alternative implementations, however, the reception operation 302 may include an operation 403 for receiving the request via at least one of a wireless network and a wired network as depicted in FIG. 4a. For instance, the network interface reception module 202* (e.g., network interface reception module 202 or network interface reception module 202') of the server 10 of FIG. 1b or the local source user device 20' of FIG. 1d receiving the request 12* (e.g., request 12 or request 12') via at least one of wireless network and a wired network 50*.

Various types of personalized plan 16* may be requested via the reception operation 302 of FIG. 3 in various alternative implementations. For example, in some implementations, the reception operation 302 may include an operation 404 for receiving a request for a personalized plan designed to facilitate an end user to achieve one or more outcomes related to athletics as depicted in FIG. 4a. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more outcomes related to athletics (e.g., an athletic skill or result such as being able to pitch a curve ball or running a mile under 6 minutes) when, for example, one or more emulatable aspects of the personalized plan 16* are emulated. Note again that in various alternative implementations, the request 12* may not specifically identify the one or more outcomes, but instead, may merely identify a source user 2*.

In some implementations, the reception operation 302 may include an operation 405 for receiving a request for a personalized plan designed to facilitate an end user to achieve one or more outcomes relating to games as depicted in FIG. 4a. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more outcomes related to games (e.g., a gaming skill or result relating to playing chess or a video/electronic game) when, for example, one or more emulatable aspects of the personalized plan 16* are emulated.

In some implementations, the reception operation 302 may include an operation 406 for receiving a request for a personalized plan designed to facilitate an end user to achieve one or more work related outcomes as depicted in FIG. 4a. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more work-related outcomes (e.g., obtaining a promotion, work related skills such as computer skills, interpersonal skills, and so forth) when, for example, one or more emulatable aspects of the personalized plan 16* are emulated.

In some implementations, the reception operation 302 may include an operation 407 for receiving a request for a personalized plan designed to facilitate an end user to achieve one or more social related outcomes as depicted in FIG. 4a. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more social related outcomes (e.g., having many friends, participating in many social activities, interpersonal skills such as public speaking, and so forth) when, for example, one or more emulatable aspects of the personalized plan 16* are emulated.

In some implementations, the reception operation 302 may include an operation 408 for receiving a request for a personalized plan designed to facilitate an end user to achieve one or more leisure related outcomes as depicted in FIG. 4a. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more leisure related outcomes (e.g., going on a vacation or being available to take a vacation, having or setting aside time to read a novel, and so forth) when, for example, one or more emulatable aspects of the personalized plan 16* are emulated.

In some implementations, the reception operation 302 may include an operation 409 for receiving a request for a personalized plan designed to facilitate an end user to achieve one or more health or medical related outcomes as depicted in FIG. 4a. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more health or medical related outcomes (e.g., reducing blood pressure or blood glucose levels, weight loss, increase red blood cell count, improve recovery from an illness such as cancer, and so forth) when, for example, one or more emulatable aspects of the personalized plan 16* are emulated.

In some implementations, the reception operation 302 may include an operation 410 for receiving a request for a personalized plan designed to facilitate an end user to achieve one or more sexual intimacy outcomes as depicted in FIG. 4a. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more sexual intimacy outcomes (e.g., increased sexual activities, increased sexual performance, and so forth) when, for example, one or more emulatable aspects of the personalized plan 16* are emulated.

Figure 4B:
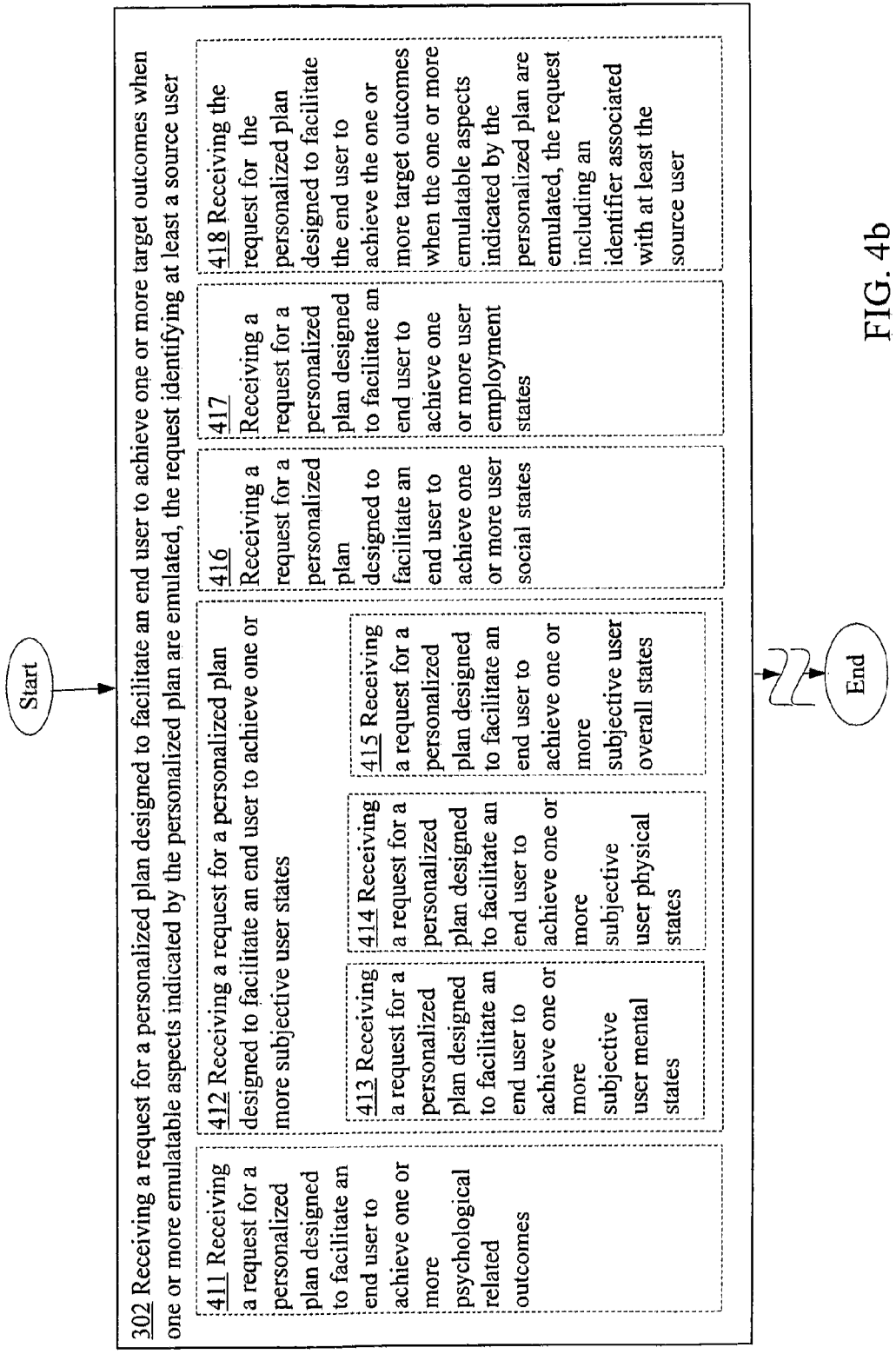
FIG. 4b is a high-level logic flowchart of a process depicting alternate implementations of the reception operation 302 of FIG. 3.

In some implementations, the reception operation 302 may include an operation 411 for receiving a request for a personalized plan designed to facilitate an end user to achieve one or more psychological related outcomes as depicted in FIG. 4b. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more psychological related outcomes (e.g., easing of a phobia, hostile feeling towards a person or a group, and so forth) when, for example, one or more emulatable aspects of the personalized plan 16* are emulated.

In some implementations, the reception operation 302 may include an operation 412 for receiving a request for a personalized plan designed to facilitate an end user to achieve one or more subjective user states as depicted in FIG. 4b. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more subjective user states when, for example, one or more emulatable aspects of the personalized plan 16* are emulated. A subjective user state may be any user state that may generally only be subjectively indicated by a user. The requested personalized plan 16* may be designed to facilitate an end user 4* to achieve various types of subjective user states.

For example, in some implementations, operation 412 may further include an operation 413 for receiving a request for a personalized plan designed to facilitate an end user to achieve one or more subjective user mental states as depicted in FIG. 4b. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more subjective user mental states (e.g., happiness, calmness, alertness, and so forth) when, for example, one or more emulatable aspects of the personalized plan 16* are emulated.

In some implementations, operation 412 may include an operation 414 for receiving a request for a personalized plan designed to facilitate an end user to achieve one or more subjective user physical states as depicted in FIG. 4b. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more subjective user physical states (e.g., feeling energized, being pain-free, being able to see and/or hear well, and so forth) when, for example, one or more emulatable aspects of the personalized plan 16* are emulated.

In some implementations, operation 412 may include an operation 415 for receiving a request for a personalized plan designed to facilitate an end user to achieve one or more subjective user overall states as depicted in FIG. 4b. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more subjective user overall states (e.g., "good," "bad," "well," "available," "busy," and so forth) when, for example, one or more emulatable aspects of the personalized plan 16* are emulated.

In some implementations, the reception operation 302 may include an operation 416 for receiving a request for a personalized plan designed to facilitate an end user to achieve one or more user social states as depicted in FIG. 4b. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more social states (e.g., being available for marriage, belonging to a higher social class, and so forth) when, for example, one or more emulatable aspects of the personalized plan 16* are emulated.

In some implementations, the reception operation 302 may include an operation 417 for receiving a request for a personalized plan designed to facilitate an end user to achieve one or more user employment states as depicted in FIG. 4b. For instance, the request reception module 102* of the server 10 of FIG. 1b, the local source user device 20' of FIG. 1d, or the local end user device 30" of FIG. 1f receiving a request 12* for a personalized plan 16* designed to facilitate an end user 4* to achieve one or more user employment states (e.g., being employed, having or obtaining an employment position such as a management position, having or developing a particular reputation at work, and so forth) when, for example, one or more emulatable aspects of the personalized plan 16* are emulated.

In order to identify the source user 2*, in some implementations, the request 12* received through the reception operation 302 of FIG. 3 may include an identifier for the source user 2*. For example, in some implementations, the reception operation 302 may include an operation 418 for receiving the request for the personalized plan designed to facilitate the end user to achieve the one or more target outcomes when the one or more emulatable aspects indicated by the personalized plan are emulated, the request including an identifier associated with at least the source user as depicted in FIG. 4b. For instance, the request reception module 102* of the server 10 of FIG. 1b, the local source user device 20' of FIG. 1d, or the local end user device 30" of FIG. 1f receiving the request 12* for the personalized plan 16* designed to facilitate the end user 4* to achieve the one or more target outcomes when the one or more emulatable aspects indicated by the personalized plan 16* are emulated, the request 12* including an identifier (e.g., an "actual" name, a user name, a title or position such as CEO or administrative assistant, accomplishment such as "winner," class such as professional football player, an image of the source user's face, an RFID identity, an avatar identity, voice recognition identification, retinal scan identification, digital fingerprint identification, credit card, social security number, and so forth) associated with at least the source user 2*.

Figure 4C:
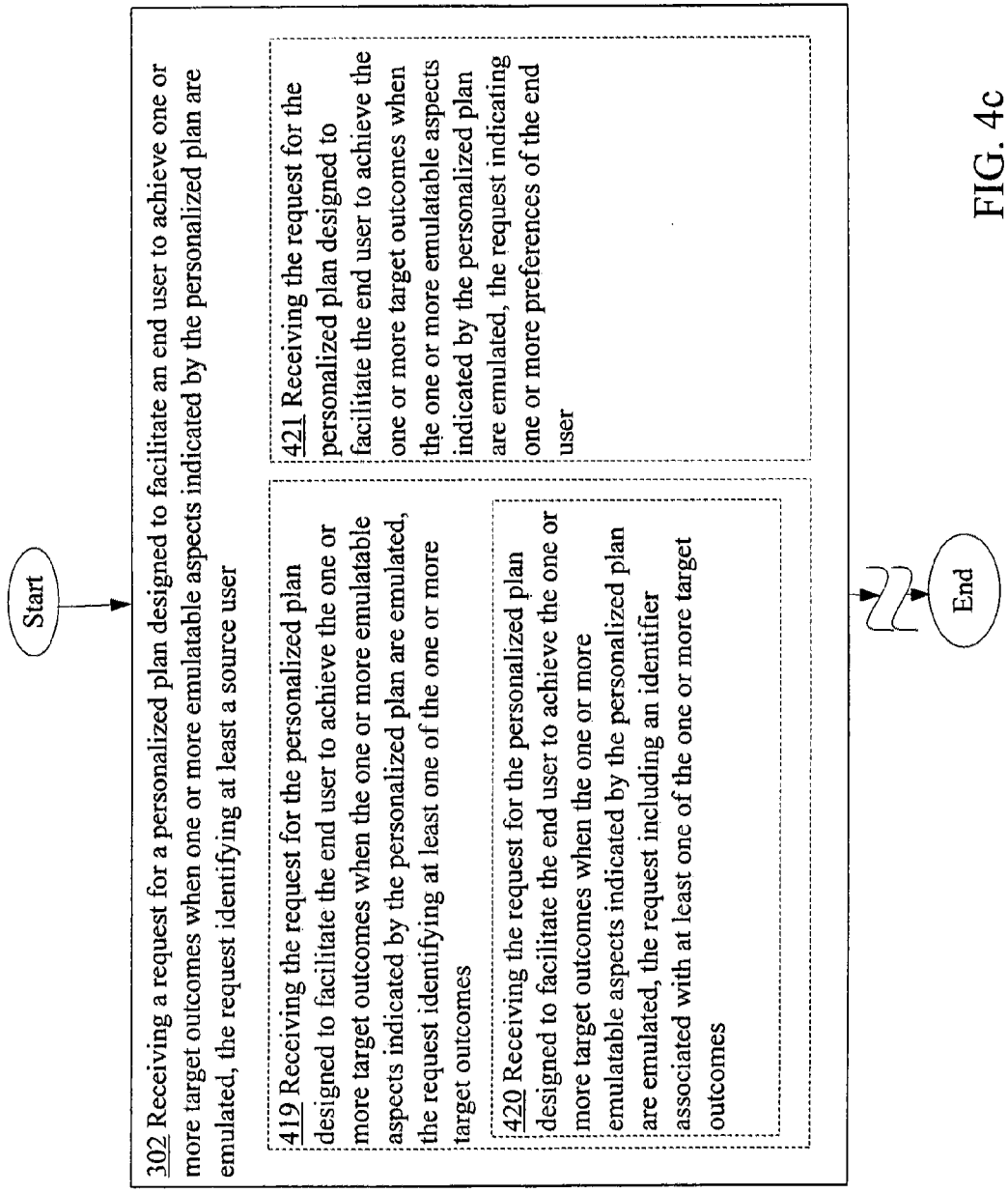
FIG. 4c is a high-level logic flowchart of a process depicting alternate implementations of the reception operation 302 of FIG. 3.

In some cases, the request 12*received through the reception operation 302 of FIG. 3 may identify at least one of the target outcomes of the personalized plan 16*. For example, in some implementations, the reception operation 302 may include an operation 419 for receiving the request for the personalized plan designed to facilitate the end user to achieve the one or more target outcomes when the one or more emulatable aspects indicated by the personalized plan are emulated, the request identifying at least one of the one or more target outcomes as depicted in FIG. 4c. For instance, the request reception module 102* of the server 10 of FIG. 1b, the local source user device 20' of FIG. 1d, or the local end user device 30" of FIG. 1f receiving the request 12* for the personalized plan 16* designed to facilitate the end user 4* to achieve one or more target outcomes when one or more emulatable aspects indicated by the personalized plan 16* are emulated, the request 12* identifying at least one of the one or more target outcomes.

In some cases, operation 419 may further include an operation 420 for receiving the request for the personalized plan designed to facilitate the end user to achieve the one or more target outcomes when the one or more emulatable aspects indicated by the personalized plan are emulated, the request including an identifier associated with at least one of the one or more target outcomes as depicted in FIG. 4c. For instance, the request reception module 102* of the server 10 of FIG. 1b, the local source user device 20' of FIG. 1d, or the local end user device 30" of FIG. 1f receiving the request 12* for the personalized plan 16* designed to facilitate the end user 4* to achieve the one or more target outcomes when the one or more emulatable aspects indicated by the personalized plan 16* are emulated, the request 12*including an identifier (e.g., a description, a name, a symbolic representation, an image of the outcome as physically displayed by, for example, the source user 2* or a third party 6*, and so forth) associated with at least one of the one or more target outcomes.

The request 12* received through the reception operation 302 of FIG. 3 may indicate other types of information in various alternative implementations. For example, in some implementations, operation 302 may include an operation 421 for receiving the request for the personalized plan designed to facilitate the end user to achieve the one or more target outcomes when the one or more emulatable aspects indicated by the personalized plan are emulated, the request indicating one or more preferences of the end user as depicted in FIG. 4c. For instance, the request reception module 102* of the server 10 of FIG. 1b, the local source user device 20' of FIG. 1d, or the local end user device 30" of FIG. 1f receiving the request 12* for a personalized plan 16* designed to facilitate an end user 4* to achieve one or more target outcomes when one or more emulatable aspects indicated by the personalized plan 16* are emulated, the request 12* indicating one or more preferences (e.g., prefer not to jog, prefer not to wake-up early, prefer not to consume certain items, and so forth) of the end user 4*.

Figure 4D:
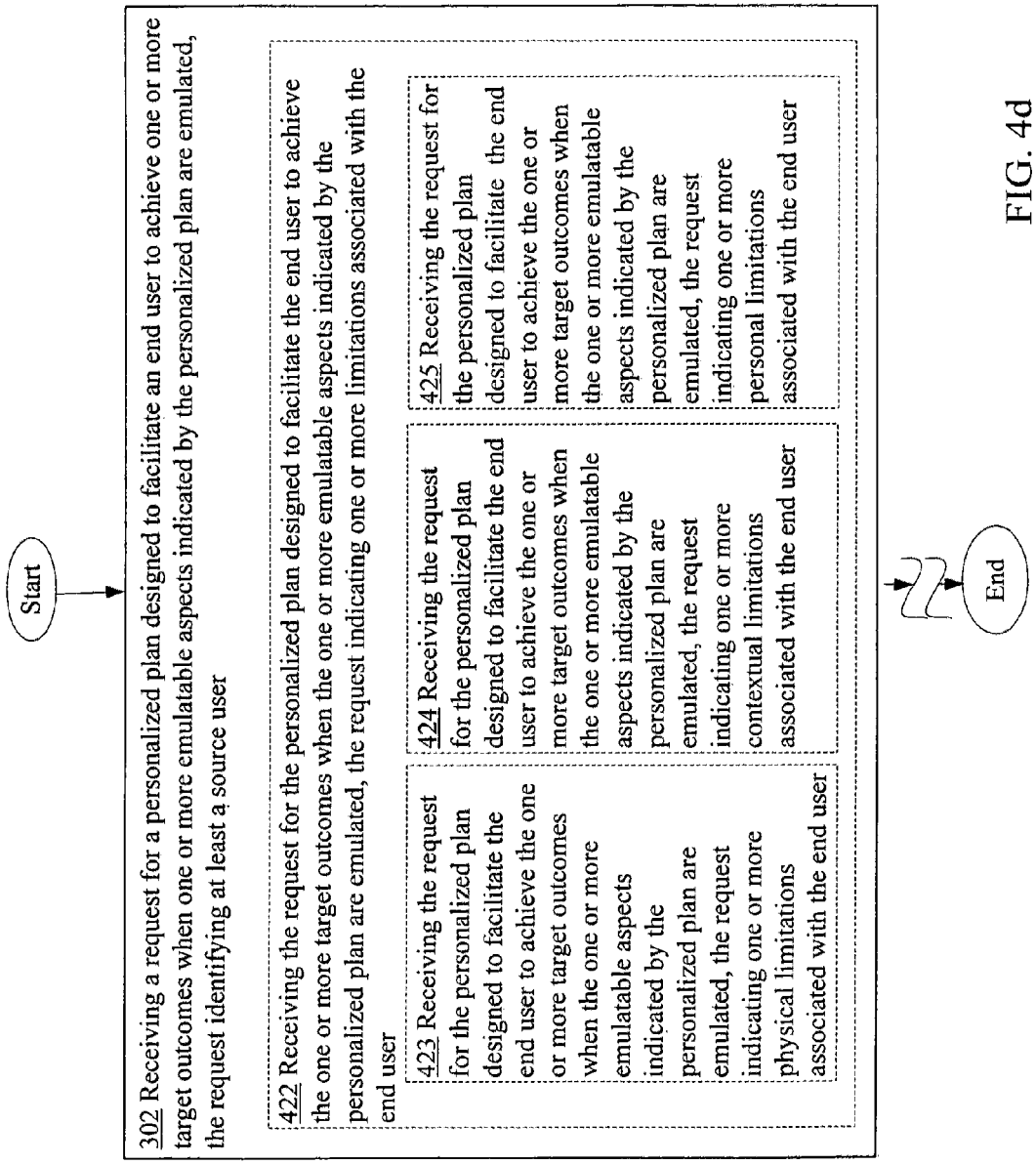
FIG. 4d is a high-level logic flowchart of a process depicting alternate implementations of the reception operation 302 of FIG. 3.

In some implementations, the reception operation 302 may include an operation 422 for receiving the request for the personalized plan designed to facilitate the end user to achieve the one or more target outcomes when the one or more emulatable aspects indicated by the personalized plan are emulated, the request indicating one or more limitations associated with the end user as depicted by FIG. 4d. For instance, the request reception module 102* of the server 10 of FIG. 1b, the local source user device 20' of FIG. 1d, or the local end user device 30" of FIG. 1f receiving the request 12* for a personalized plan 16* designed to facilitate an end user 4* to achieve one or more target outcomes when one or more emulatable aspects indicated by the personalized plan 16* are emulated, the request 12* indicating one or more limitations (e.g., physical or mental handicaps, scheduling limitations, logistical limitations, and so forth) associated with the end user 4*.

Operation 422, in turn, may further include an operation 423 for receiving the request for the personalized plan designed to facilitate the end user to achieve the one or more target outcomes when the one or more emulatable aspects indicated by the personalized plan are emulated, the request indicating one or more physical limitations associated with the end user as depicted in FIG. 4d. For instance, the request reception module 102* of the server 10 of FIG. 1b, the local source user device 20' of FIG. 1d, or the local end user device 30" of FIG. 1f receiving the request 12* for a personalized plan 16* designed to facilitate an end user 4* to achieve one or more target outcomes when one or more emulatable aspects indicated by the personalized plan 16* are emulated, the request 12* indicating one or more physical limitations (e.g., visual or hearing limitations, physical movement limitations such as those related to a paraplegic, physical characteristic limitations such as height, weight, and so forth, related to the end user 4*, physiological limitations such as cholesterol levels, and so forth) associated with the end user 4*.

In the same or different implementations, operation 422 may include an operation 424 for receiving the request for the personalized plan designed to facilitate the end user to achieve the one or more target outcomes when the one or more emulatable aspects indicated by the personalized plan are emulated, the request indicating one or more contextual limitations associated with the end user as depicted in FIG. 4d. For instance, the request reception module 102* of the server 10 (of FIG. 1b), the local source user device 20' (of FIG. 1d), or the local end user device 30" (of FIG. 1f) receiving the request 12* for a personalized plan 16* designed to facilitate an end user 4* to achieve one or more target outcomes when one or more emulatable aspects indicated by the personalized plan 16* are emulated, the request 12* indicating one or more contextual limitations (e.g., scheduling limitations, geographical limitations, asset limitations such as lack of particular equipment or facilities, and so forth) associated with the end user 4*.

In the same or different implementations, operation 422 may include an operation 425 for receiving the request for the personalized plan designed to facilitate the end user to achieve the one or more target outcomes when the one or more emulatable aspects indicated by the personalized plan are emulated, the request indicating one or more personal limitations associated with the end user as depicted in FIG. 4d. For instance, the request reception module 102* of the server 10 of FIG. 1b, the local source user device 20' of FIG. 1d, or the local end user device 30" of FIG. 1f receiving the request 12* for a personalized plan 16* designed to facilitate an end user 4* to achieve one or more target outcomes when one or more emulatable aspects indicated by the personalized plan 16* are emulated, the request 12* indicating one or more personal limitations (e.g., religious beliefs, dietary beliefs, phobias, personal prejudices, limitations related to personal experiences, personal work schedule, family dynamics or circumstances, and so forth) associated with the end user 4\*.

Figure 4E:
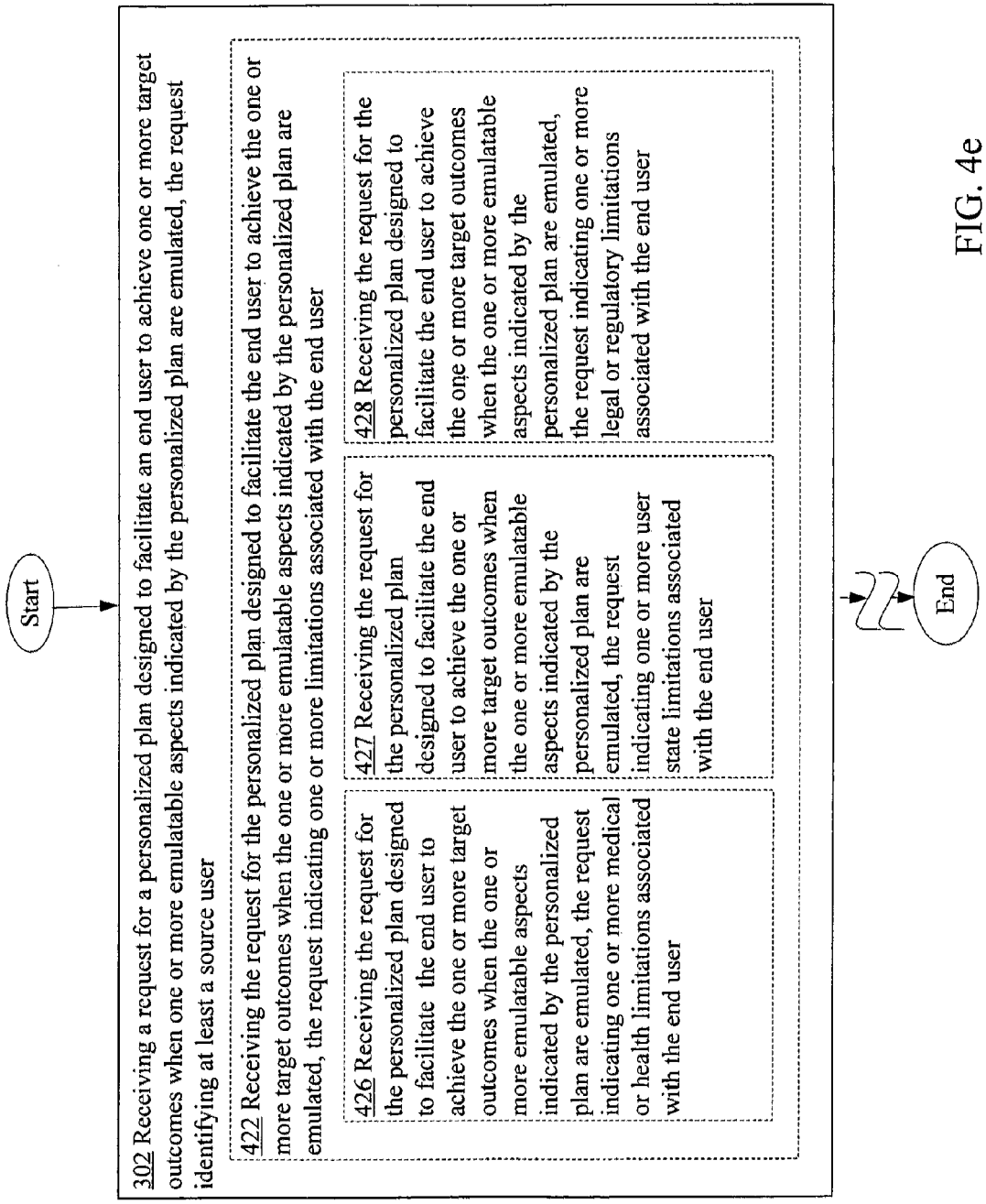
FIG. 4e is a high-level logic flowchart of a process depicting alternate implementations of the reception operation 302 of FIG. 3.

In the same or different implementations, operation 422 may include an operation 426 for receiving the request for the personalized plan designed to facilitate the end user to achieve the one or more target outcomes when the one or more emulatable aspects indicated by the personalized plan are emulated, the request indicating one or more medical or health limitations associated with the end user as depicted in FIG. 4e. For instance, the request reception module 102\* of the server 10 of FIG. 1b, the local source user device 20' of FIG. 1d, or the local end user device 30" of FIG. 1f receiving the request 12\* for a personalized plan 16\* designed to facilitate an end user 4\* to achieve one or more target outcomes when one or more emulatable aspects indicated by the personalized plan 16\* are emulated, the request 12\* indicating one or more medical or health limitations (e.g., medical limitations as limitations resulting from an illness or treatment of the illness including physical limitations due to cancer or treatment thereof, health limitations related to the physical conditioning of the end user 4\*, genetic limitations, and so forth) associated with the end user 4\*.

In the same or different implementations, operation 422 may include an operation 427 for receiving the request for the personalized plan designed to facilitate the end user to achieve the one or more target outcomes when the one or more emulatable aspects indicated by the personalized plan are emulated, the request indicating one or more user state limitations associated with the end user as depicted in FIG. 4e. For instance, the request reception module 102\* of the server 10 of FIG. 1b, the local source user device 20' of FIG. 1d, or the local end user device 30" of FIG. 1f receiving the request 12\* for a personalized plan 16\* designed to facilitate an end user 4\* to achieve one or more target outcomes when one or more emulatable aspects indicated by the personalized plan 16\* are emulated, the request 12\* indicating one or more user state limitations (e.g., end user 4\* is married, end user 4\* is in mourning, end user 4\* is unemployed, end user 4\* is a vegan, and so forth) associated with the end user 4\*.

In the same or different implementations, operation 422 may include an operation 428 for receiving the request for the personalized plan designed to facilitate the end user to achieve the one or more target outcomes when the one or more emulatable aspects indicated by the personalized plan are emulated, the request indicating one or more legal or regulatory limitations associated with the end user as depicted in FIG. 4e. For instance, the request reception module 102\* of the server 10 of FIG. 1b, the local source user device 20' of FIG. 1d, or the local end user device 30" of FIG. 1f receiving the request 12\* for a personalized plan 16\* designed to facilitate an end user 4\* to achieve one or more target outcomes when one or more emulatable aspects indicated by the personalized plan 16\* are emulated, the request 12\* indicating one or more legal or regulatory limitations (e.g., drug regulations, laws related to conduct, and so forth) associated with the end user 4\*. Note that the legal or regulatory limitations between where the source user 2\* resides and where the end user 4\* resides may differ, and therefore, such information may be useful in developing a personalized plan 16\*.

Figure 5A:
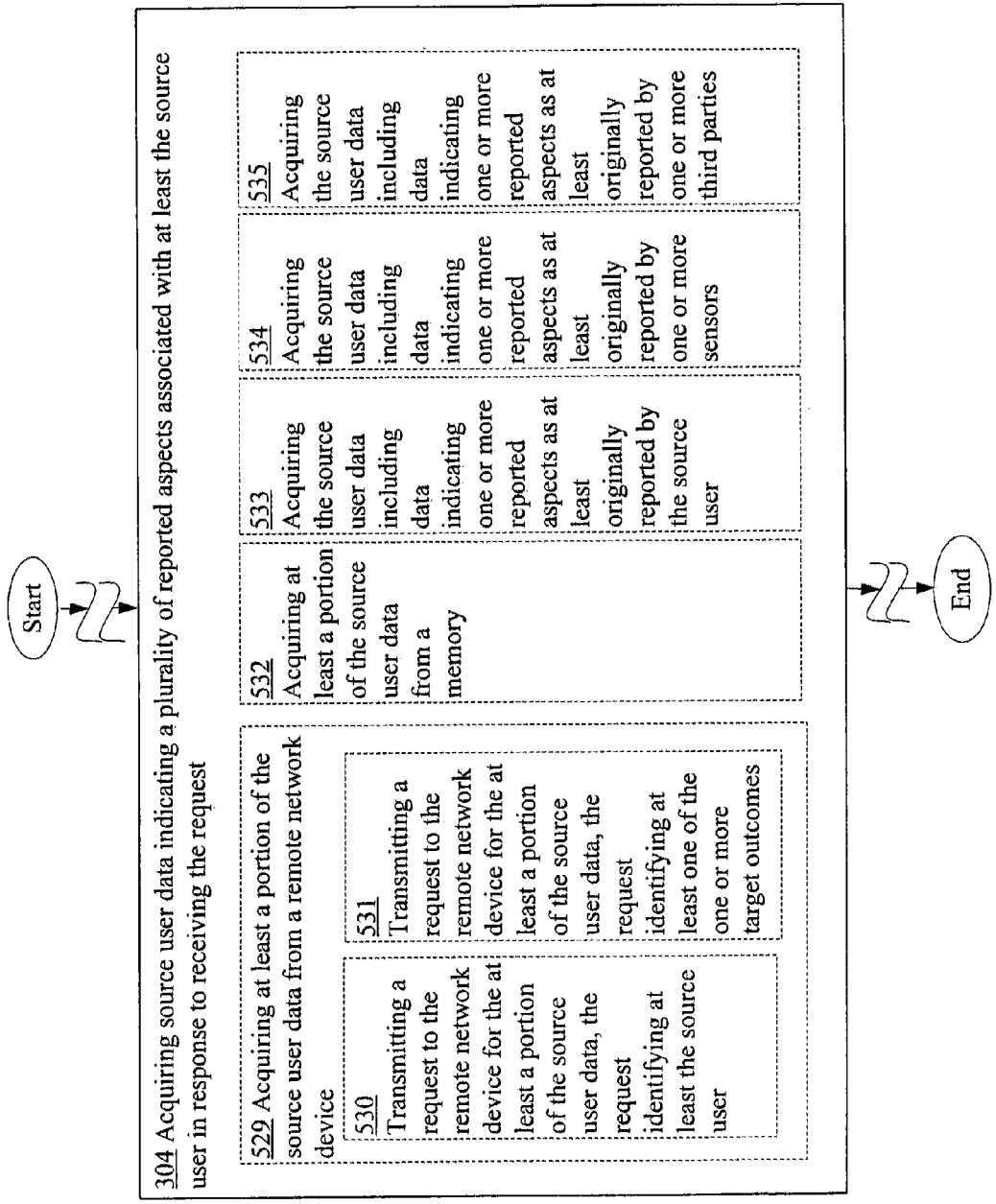
FIG. 5a is a high-level logic flowchart of a process depicting alternate implementations of the acquisition operation 304 of FIG. 3.

Referring back to FIG. 3, the acquisition operation 304 may be executed in a variety of different manners in various alternative implementations. For instance, the source user data 14\* acquired through the acquisition operation 304 may be acquired from different sources and/or may have at least originated from different sources. For example, in some implementations, the acquisition operation 304 may include an operation 529 for acquiring at least a portion of the source user data from a remote network device as depicted in FIG. 5a. For instance, the source user data acquisition module 104\* of the server 10 of FIG. 1b, the local source user device 20' of FIG. 1d, or the local end user device 30" of FIG. 1f acquiring at least a portion of the source user data 14\* (e.g., log data such as social networking entry data or diary data) from a remote network device (e.g., in embodiments in which operational flow 300 is implemented at a server 10 as depicted in FIGS. 1a and 1b, at least a portion of the source user data 14 may be acquired from a local source user device 20, from one or more third party devices such as other source user devices, and/or from one or more sensors 40).

In some implementations, operation 529 may, in turn, include an operation 530 for transmitting a request to the remote network device for the at least a portion of the source user data, the request identifying at least the source user as depicted in FIG. 5a. For instance, the request transmission module 204\* of the server 10 of FIG. 1b, the local source user device 20' of FIG. 1d, or the local end user device 30" of FIG. 1f transmitting (e.g., via wireless network and/or wired network 50) a request to the remote network device for the at least a portion of the source user data 14\*, the request identifying at least the source user 2\*. For example, in embodiments in which the operational flow 300 is being executed at a local end user device 30" (e.g., FIGS. 1e and 1f), the request transmission module 204" of the local end user device 30" may transmit to the server 10", the local source user device 20", and/or one or more sensors 40" a request for at least a portion of the source user data 14", the request identifying at least the source user 2". In various implementations, the source user data reception module 206\* of the server 10 of FIG. 1b, the local source user device 20' of FIG. 1d, or the local end user device 30" of FIG. 1f may then receive the requested source user data 14\*.

In the same or different implementations, operation 529 may include an operation 531 for transmitting a request to the remote network device for the at least a portion of the source user data, the request identifying at least one of the one or more target outcomes as depicted in FIG. 5a. For instance, the request transmission module 204\* of the server 10 of FIG. 1b, the local source user device 20' of FIG. 1d, or the local end user device 30" of FIG. 1f transmitting (e.g., via wireless network and/or wired network 50) a request to the remote network device for the at least a portion of the source user data 14\*, the request identifying at least one of the one or more target outcomes. For example, in embodiments in which the operational flow 300 is being executed at a local source user device 20' (e.g., FIGS. 1c and 1d), the request transmission module 204' of the local source user device 20' may transmit to the server 10' and/or one or more sensors 40' a request for at least a portion of the source user data 14", the request identifying at least one of the one or more target outcomes of the personalized plan 16'.

In some implementations, the acquisition operation 304 may include an operation 532 for acquiring at least a portion of the source user data from a memory as depicted in FIG. 5a. For instance, the source user data acquisition module 104\* of the server 10 of FIG. 1b or the local source user device 20' of FIG. 1d acquiring at least a portion of the source user data 14\* from a memory 116\* (e.g., flash memory, volatile memory, non-volatile memory, cache memory, and so forth).

In some implementations, the acquisition operation 304 may include an operation 533 for acquiring the source user data including data indicating one or more reported aspects as at least originally reported by the source user as depicted in FIG. 5a. For instance, the source user data acquisition module 104* of the server 10 of FIG. 1b, the local source user device 20' of FIG. 1d, or the local end user device 30" of FIG. 1f acquiring the source user data 14* including data indicating one or more reported aspects as at least originally reported by the source user 2*.

In some implementations, the acquisition operation 304 may include an operation 534 for acquiring the source user data including data indicating one or more reported aspects as at least originally reported by one or more sensors as depicted in FIG. 5a. For instance, the source user data acquisition module 104* of the server 10 of FIG. 1b, the local source user device 20' of FIG. 1d, or the local end user device 30" of FIG. 1f acquiring the source user data 14* including data indicating one or more reported aspects as at least originally reported by one or more sensors 40* (e.g., physiological sensing devices such as blood pressure or blood glucose sensors, sensors to sense activities of a subject such as pedometers, GPSs, exercise machine sensors, and accelerometers, sensors to measure environmental conditions such as thermometers or air quality sensors, and so forth).

In some implementations, the acquisition operation 304 may include an operation 535 for acquiring the source user data including data indicating one or more reported aspects as at least originally reported by one or more third parties as depicted in FIG. 5a. For instance, the source user data acquisition module 104* of the server 10 (of FIG. 1b), the local source user device 20' (of FIG. 1d), or the local end user device 30" (of FIG. 1f) acquiring the source user data 14* including data indicating one or more reported aspects as at least originally reported by one or more third parties 6* (e.g., other end users, spouses, friends, employers, and so forth).

Figure 5B:
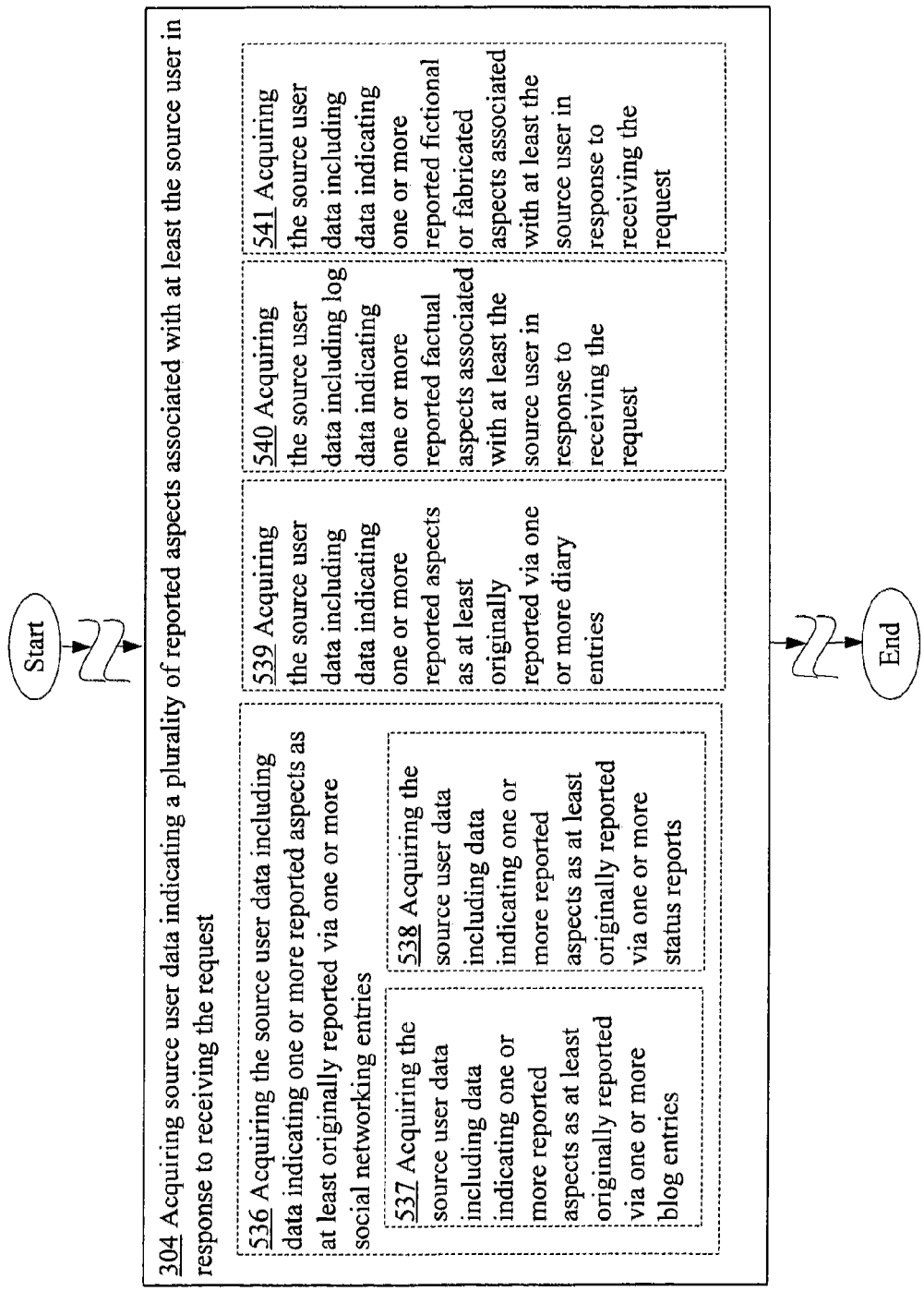
FIG. 5b is a high-level logic flowchart of a process depicting alternate implementations of the acquisition operation 304 of FIG. 3.

In some implementations, the acquisition operation 304 may include an operation 536 for acquiring the source user data including data indicating one or more reported aspects as at least originally reported via one or more social networking entries as depicted in FIG. 5b. For instance, the source user data acquisition module 104* of the server 10 of FIG. 1b, the local source user device 20' of FIG. 1d, or the local end user device 30" of FIG. 1f acquiring the source user data 14* including data (e.g., log data) indicating one or more reported aspects as at least originally reported via one or more social networking entries.

In various implementations, operation 536 may further include an operation 537 for acquiring the source user data including data indicating one or more reported aspects as at least originally reported via one or more blog entries as depicted in FIG. 5b. For instance, the source user data acquisition module 104* of the server 10 of FIG. 1b, the local source user device 20' of FIG. 1d, or the local end user device 30" of FIG. 1f acquiring the source user data 14* including data (e.g., log data) indicating one or more reported aspects as at least originally reported via one or more blog (e.g., microblog) entries (e.g., as entered by the source user 2* or by a third party 6*).

In some implementations, operation 536 may further include an operation 538 for acquiring the source user data including data indicating one or more reported aspects as at least originally reported via one or more status reports as depicted in FIG. 5b. For instance, the source user data acquisition module 104* of the server 10 of FIG. 1b, the local source user device 20' of FIG. 1d, or the local end user device 30" of FIG. 1f acquiring the source user data 14* including data (e.g., log data) indicating one or more reported aspects as at least originally reported via one or more status reports (e.g., as reported by the source user 2* or by a third party 6*).

In various implementations, the acquisition operation 304 may include an operation 539 for acquiring the source user data including data indicating one or more reported aspects as at least originally reported via one or more diary entries as depicted in FIG. 5b. For instance, the source user data acquisition module 104* of the server 10 of FIG. 1b, the local source user device 20' of FIG. 1d, or the local end user device 30" of FIG. 1f acquiring the source user data 14* including data (e.g., log data) indicating one or more reported aspects as at least originally reported via one or more diary entries (e.g., as entered by the source user 2* or by a third party 6*). Note that in some cases, diary entries may also include data provided by one or more sensors 40*.

In some implementations, the acquisition operation 304 may include an operation 540 for acquiring the source user data including log data indicating one or more reported factual aspects associated with at least the source user in response to receiving the request as depicted in FIG. 5b. For instance, the source user data acquisition module 104* of the server 10 of FIG. 1b, the local source user device 20' of FIG. 1d, or the local end user device 30" of FIG. 1f acquiring the source user data 14* including log data indicating one or more reported factual aspects (e.g., rather than fictional or imaginary aspects) associated with at least the source user 2* in response to receiving the request 12*.

In some implementations, the acquisition operation 304 may include an operation 541 for acquiring the source user data including data indicating one or more reported fictional or fabricated aspects associated with at least the source user in response to receiving the request as depicted in FIG. 5b. For instance, the source user data acquisition module 104* of the server 10 of FIG. 1b, the local source user device 20' of FIG. 1d, or the local end user device 30" of FIG. 1f acquiring the source user data 14* including data indicating one or more reported fictional or fabricated aspects associated with at least the source user 2* in response to receiving the request 12*.

Figure 5C:
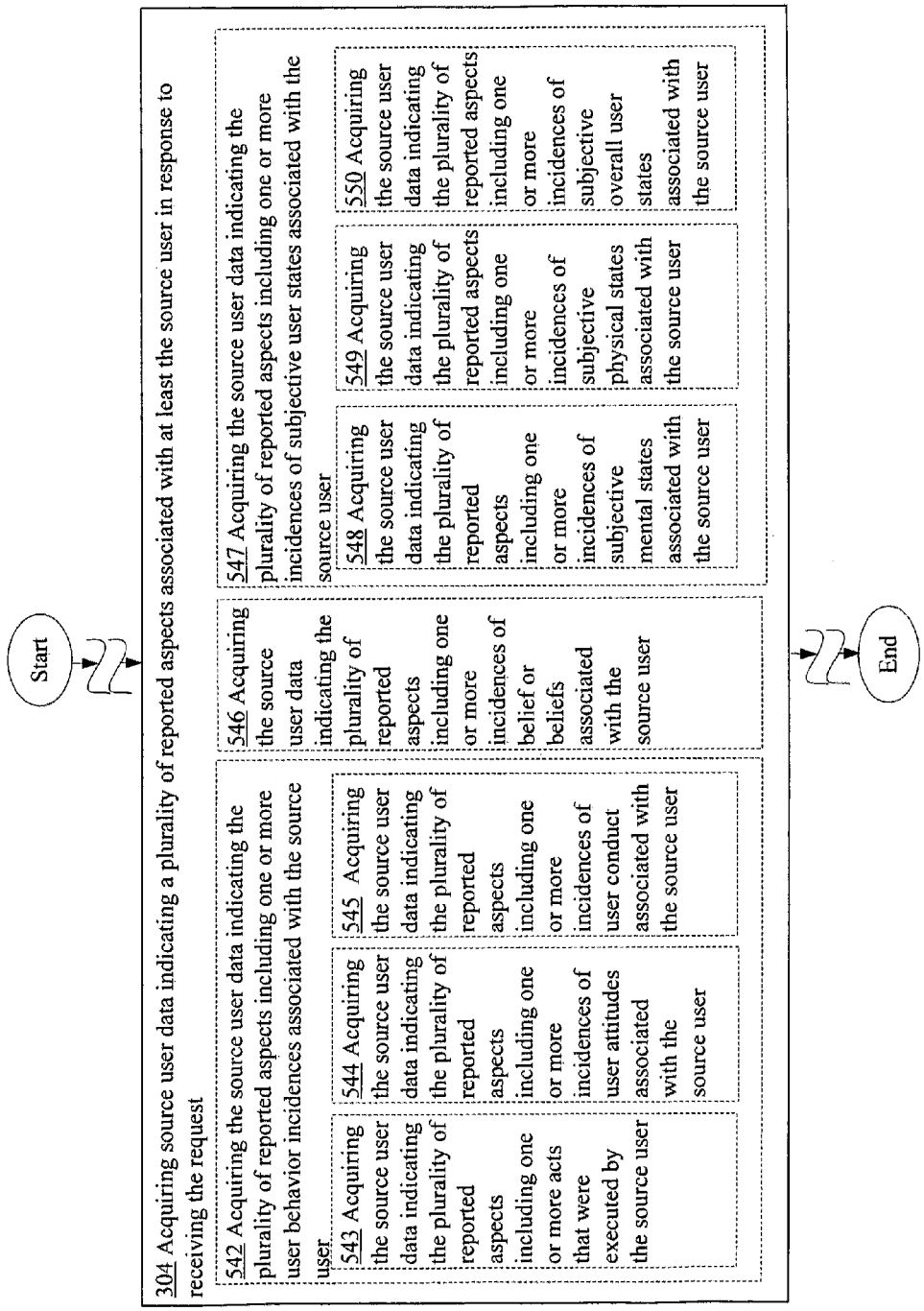
FIG. 5c is a high-level logic flowchart of a process depicting alternate implementations of the acquisition operation 304 of FIG. 3.

Various types of reported aspects associated with a source user 2* may be indicated by the source user data 14* acquired through the acquisition operation 304 of FIG. 3. For example, in some implementations, the acquisition operation 304 may include an operation 542 for acquiring the source user data indicating the plurality of reported aspects including one or more user behavior incidences associated with the source user as depicted in FIG. 5c. For instance, the source user data acquisition module 104* of the server 10 of FIG. 1b, the local source user device 20' of FIG. 1d, or the local end user device 30" of FIG. 1f acquiring the source user data 14* indicating the plurality of reported aspects including one or more user behavior incidences (e.g., dietary behavior, exercise or athletic behavior, social behavior, work behavior, sexual behavior, and so forth) associated with the source user 2*.

Operation 542, in turn, may include one or more additional operations in various alternative implementations. For example, in some implementations, operation 542 may include an operation 543 for acquiring the source user data indicating the plurality of reported aspects including one or more acts that were executed by the source user as depicted in FIG. 5c. For instance, the source user data acquisition module 104* of the server 10 of FIG. 1b, the local source user device 20' of FIG. 1d, or the local end user device 30" of FIG. 1f acquiring the source user data 14* indicating the plurality of reported aspects including one or more acts (e.g., exercising, eating, driving, sleeping, waking-up early, reading, studying, and so forth) that were executed by the source user 2*.

In the same or different implementations, operation 542 may include an operation 544 for acquiring the source user data indicating the plurality of reported aspects including one or more incidences of user attitudes associated with the source user as depicted in FIG. 5c. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of user attitudes (e.g., anger, happiness, skeptical, alert, hostile, accepting, indifference, and so forth) associated with the source user 2*.

In the same or different implementations, operation 542 may include an operation 545 for acquiring the source user data indicating the plurality of reported aspects including one or more incidences of user conduct associated with the source user as depicted in FIG. 5*c*. For instance, the source user data acquisition module 104* of the server 10 (of FIG. 1*b*), the local source user device 20' (of FIG. 1*d*), or the local end user device 30" (of FIG. 1*f*) acquiring the source user data 14* indicating the plurality of reported aspects including one or more incidences of user conduct (e.g., how a source user 2* interacts with others, how a source user 2* reacts to external events, and so forth) associated with the source user 2*.

In some implementations, the acquisition operation 304 of FIG. 3 may include an operation 546 for acquiring the source user data indicating the plurality of reported aspects including one or more incidences of belief or beliefs associated with the source user as depicted in FIG. 5*c*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of belief or beliefs (e.g., religious beliefs, spiritual beliefs, dietary beliefs, and so forth) associated with the source user 2*.

In some implementations, the acquisition operation 304 may include an operation 547 for acquiring the source user data indicating the plurality of reported aspects including one or more incidences of subjective user states associated with the source user as depicted in FIG. 5*c*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of subjective user states (e.g., "rested," "well," "alert," "occupied," "relaxed," and so forth) associated with the source user 2*. For these implementations, incidences of various types of subjective user states may be indicated by the acquired source user data 14*.

For example, in some implementations, operation 547 may include an operation 548 for acquiring the source user data indicating the plurality of reported aspects including one or more incidences of subjective mental states associated with the source user as depicted in FIG. 5*c*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of subjective mental states (e.g., happy, relaxed, calm, awake or alert, and so forth) associated with the source user 2*.

In the same or different implementations, operation 547 may include an operation 549 for acquiring the source user data indicating the plurality of reported aspects including one or more incidences of subjective physical states associated with the source user as depicted in FIG. 5*c*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of subjective physical states (e.g., being fit, having endurance, being pain free, and so forth) associated with the source user 2*.

In the same or different implementations, operation 547 may include an operation 550 for acquiring the source user data indicating the plurality of reported aspects including one or more incidences of subjective overall user states associated with the source user as depicted in FIG. 5*c*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of subjective overall user states (e.g., "good," "well," "available," and so forth) associated with the source user 2*.

Figure 5D:
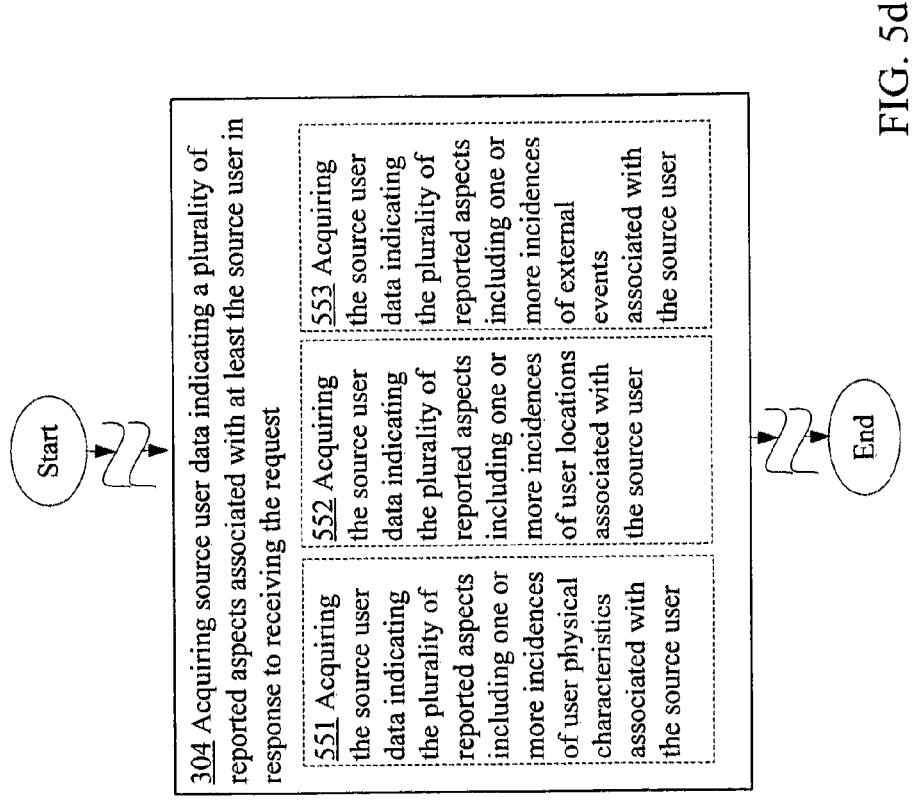
FIG. 5d is a high-level logic flowchart of a process depicting alternate implementations of the acquisition operation 304 of FIG. 3.

Incidences of other types of aspects associated with a source user 2* may also be indicated by the source user data 14* acquired through the acquisition operation 304 in various alternative implementations. For example, in some implementations, the acquisition operation 304 may include an operation 551 for acquiring the source user data indicating the plurality of reported aspects including one or more incidences of user physical characteristics associated with the source user as depicted in FIG. 5*d*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of user physical characteristics (e.g., hair color, hair length, weight loss, nail color or length, and so forth) associated with the source user 2*.

In some implementations, the acquisition operation 304 may include an operation 552 for acquiring the source user data indicating the plurality of reported aspects including one or more incidences of user locations associated with the source user as depicted in FIG. 5*d*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of user locations (e.g., home, workplace, Hawaii, the gym, and so forth) associated with the source user 2*.

In some implementations, the acquisition operation 304 may include an operation 553 for acquiring the source user data indicating the plurality of reported aspects including one or more incidences of external events associated with the source user as depicted in FIG. 5*d*. For instance, the source user data acquisition module 104* of the server 10 of FIG. 1*b*, the local source user device 20' of FIG. 1*d*, or the local end user device 30" of FIG. 1*f* acquiring the source user data 14* indicating the plurality of reported aspects including one or more incidences of external events (e.g., weather, drinking water quality, work environment, and so forth) associated with the source user 2*.

Figure 5E:
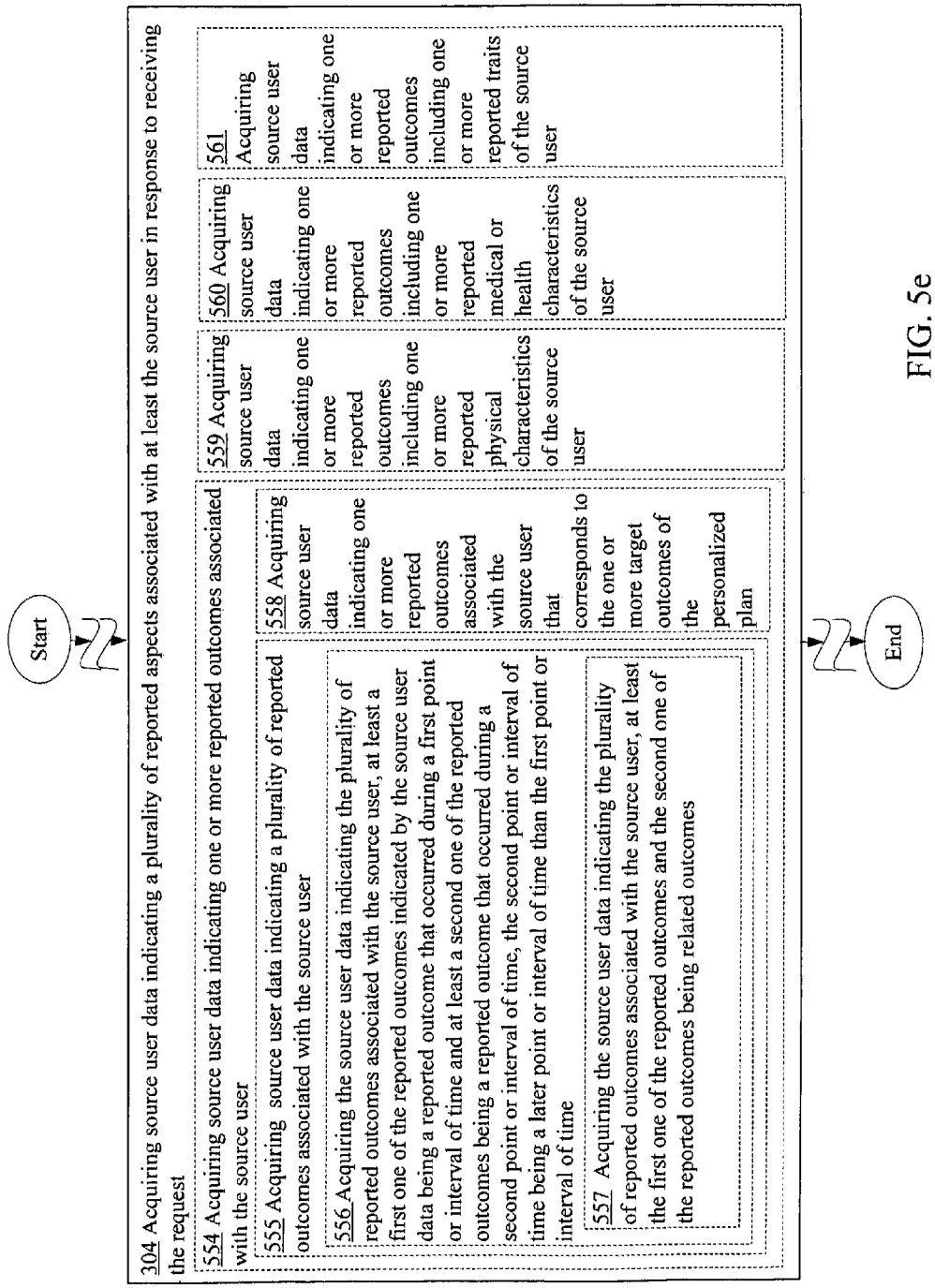
FIG. 5e is a high-level logic flowchart of a process depicting alternate implementations of the acquisition operation 304 of FIG. 3.

In addition to acquiring source user data that indicates a plurality of reported aspects associated with a source user 2*, the acquisition operation 304 of FIG. 3 may involve the acquisition of source user data that indicates other types of events. For example, in some implementations, the acquisition operation 304 may include an operation 554 for acquiring source user data indicating one or more reported outcomes associated with the source user as depicted in FIG. 5*e*. For instance, the source user data acquisition module 104* of the server 10 of FIG. 1*b*, the local source user device 20' of FIG. 1*d*, or the local end user device 30" of FIG. 1*f* acquiring source user data 14* indicating one or more reported outcomes (e.g., at least one intermediate outcome related to the final or target outcome) associated with the source user 2*.

Note that a "reported outcome" may be viewed, in some cases, as merely one type of reported aspect associated with a source user 2*. For example, the weight loss of a source user 2* at different points in time may represent reported outcomes but may also be considered reported aspects associated with the source user 2* in some cases. For these cases, the distinction with respect to a reported outcome as opposed to, for example, other types of reported aspects are that a reported outcome may be the result of or is dependent on the occurrence of other reported aspects, while other types of reported aspects may not be dependent on the occurrence of other reported aspects.

In various implementations, operation 554 may include one or more operations. For example, in some implementations, operation 554 may include an operation 555 for acquiring source user data indicating a plurality of reported outcomes associated with the source user as depicted in FIG. 5e. For instance, the source user data acquisition module 104* of the server 10 of FIG. 1b, the local source user device 20' of FIG. 1d, or the local end user device 30" of FIG. 1f acquiring source user data 14* indicating a plurality of reported outcomes (e.g., blood pressure levels or bowling scores over the course of several months) associated with the source user 2*.

In some implementations, operation 555 may further include an operation 556 for acquiring the source user data indicating the plurality of reported outcomes associated with the source user, at least a first one of the reported outcomes indicated by the source user data being a reported outcome that occurred during a first point or interval of time and at least a second one of the reported outcomes being a reported outcome that occurred during a second point or interval of time, the second point or interval of time being a later point or interval of time than the first point or interval of time as depicted in FIG. 5e. For instance, the source user data acquisition module 104* of the server 10 of FIG. 1b, the local source user device 20' of FIG. 1d, or the local end user device 30" of FIG. 1f acquiring the source user data 14* indicating the plurality of reported outcomes associated with the source user 2*, at least a first one of the reported outcomes (e.g., a bowling average of 98) indicated by the source user data 14* being a reported outcome that occurred during a first point or interval of time and at least a second one of the reported outcomes (e.g., a bowling average of 156) being a reported outcome that occurred during a second point or interval of time, the second point or interval of time (e.g., May 9, 2011) being a later point or interval of time than the first point or interval of time (e.g., Mar. 2, 2011).

Operation 556, in turn, may further include an operation 557 for acquiring the source user data indicating the plurality of reported outcomes associated with the source user, at least the first one of the reported outcomes and the second one of the reported outcomes being related outcomes as depicted in FIG. 5e. For instance, the source user data acquisition module 104* of the server 10 of FIG. 1b, the local source user device 20' of FIG. 1d, or the local end user device 30" of FIG. 1f acquiring source user data 14* indicating the plurality of reported outcomes associated with the source user 2*, at least the first one of the reported outcomes and the second one of the reported outcomes being related outcomes (e.g., same types of outcomes such as outcomes related to weight loss, outcomes related to a particular work skill such as word processing skills, outcomes related to a particular interpersonal skill such as developing new friendships, and so forth).

In various implementations, the operation 554 for acquiring source user data indicating one or more reported outcomes associated with the source user, may further include an operation 558 for acquiring source user data indicating one or more reported outcomes associated with the source user that corresponds to the one or more target outcomes of the personalized plan as depicted in FIG. 5e. For instance, the source user data acquisition module 104* of the server 10 of FIG. 1b, the local source user device 20' of FIG. 1d, or the local end user device 30" of FIG. 1f acquiring source user data 14* indicating one or more reported outcomes (e.g., a final reported outcome such as weight loss) associated with the source user 2* that corresponds to the one or more target outcomes (e.g., a target weight loss) of the personalized plan 16*.

In some implementations, the acquisition operation 304 of FIG. 3 may include an operation 559 for acquiring source user data indicating one or more reported outcomes including one or more reported physical characteristics of the source user as depicted in FIG. 5e. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported physical characteristics (e.g., weight, hair color, physiological characteristic such as hormone level or heart rate at rest, skin tone, hearing characteristic, vision characteristic, and so forth) of the source user 2*.

In some implementations, the acquisition operation 304 of FIG. 3 may include an operation 560 for acquiring source user data indicating one or more reported outcomes including one or more reported medical or health characteristics of the source user as depicted in FIG. 5e. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported medical or health characteristics (e.g., reduction in tumor size, absence of a malignant tumor, improved cardiovascular performance, and so forth) of the source user 2*.

In some implementations, the acquisition operation 304 of FIG. 3 may include an operation 561 for acquiring source user data indicating one or more reported outcomes including one or more reported traits of the source user as depicted in FIG. 5e. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported traits (e.g., mannerisms, alertness, affect, charisma, demeanor, style, number of friends, wealth, happiness, sadness, order in life, organization, control, well being, spirituality, improved communication, better personal or professional relationships, better anger management, better cognitive skills, improved vocabulary, improved problem solving skills, improved coping mechanisms, better math skills, and so forth) of the source user 2*.

Figure 5F:
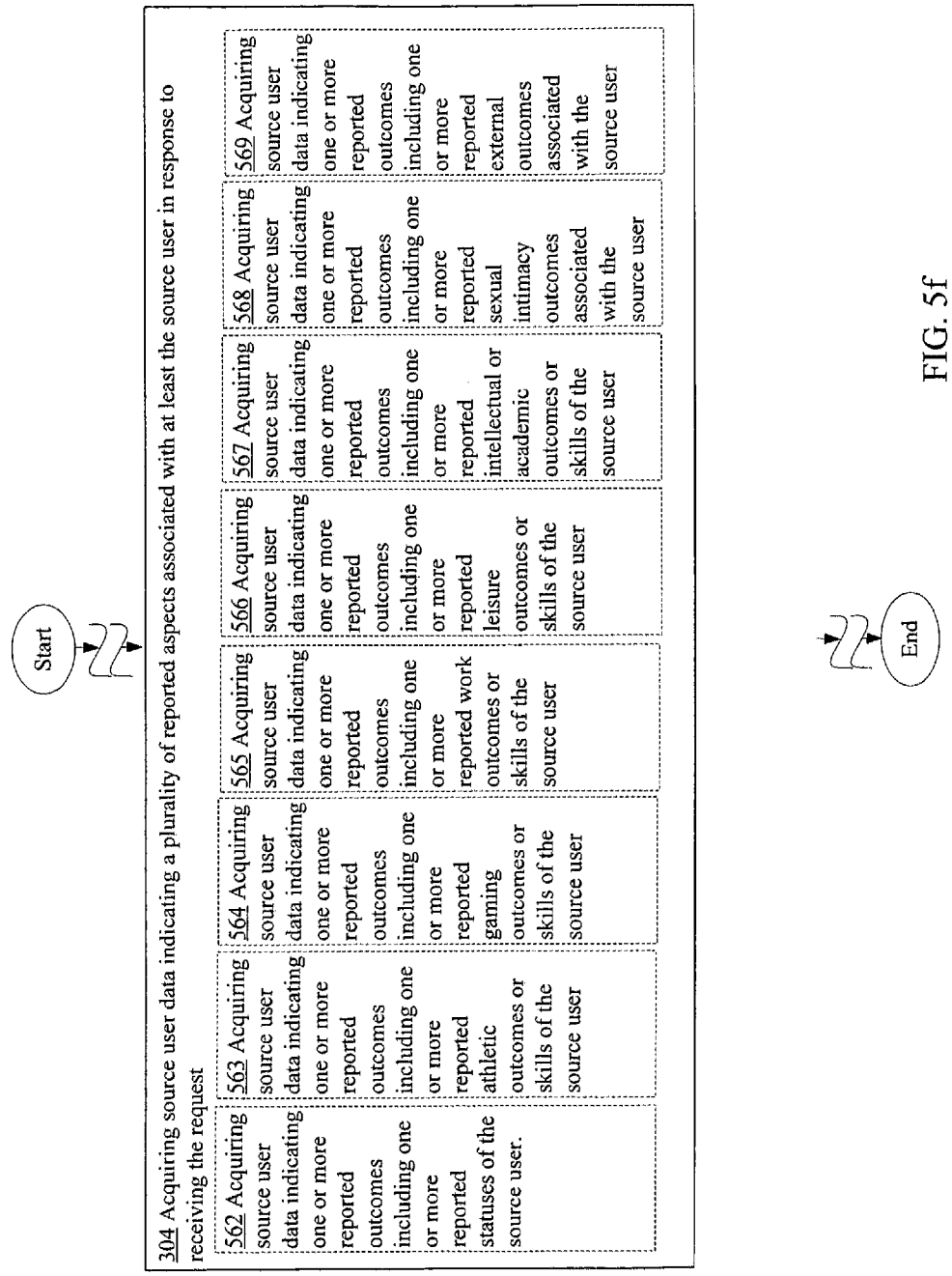
FIG. 5f is a high-level logic flowchart of a process depicting alternate implementations of the acquisition operation 304 of FIG. 3.

In some implementations, the acquisition operation 304 of FIG. 3 may include an operation 562 for acquiring source user data indicating one or more reported outcomes including one or more reported statuses of the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported statuses (e.g., availability, wellness, employment, marital, physical or mental states, and so forth) of the source user 2*.

In some implementations, the acquisition operation 304 of FIG. 3 may include an operation 563 for acquiring source user data indicating one or more reported outcomes including one or more reported athletic outcomes or skills of the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported athletic outcomes or skills (e.g., reducing golf handicap, swimming one mile, developing a curveball patch, and so forth) of the source user 2*.

In some implementations, the acquisition operation 304 of FIG. 3 may include an operation 564 for acquiring source user data indicating one or more reported outcomes including one or more reported gaming outcomes or skills of the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported gaming outcomes or skills (e.g., chess playing results, video/electronic gaming skills, and so forth) of the source user 2*.

In some implementations, the acquisition operation 304 of FIG. 3 may include an operation 565 for acquiring source user data indicating one or more reported outcomes including one or more reported work outcomes or skills of the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported work outcomes or skills (e.g., successful completion of a project, computer skills, managerial skills, and so forth) of the source user 2*.

In some implementations, the acquisition operation 304 of FIG. 3 may include an operation 566 for acquiring source user data indicating one or more reported outcomes including one or more reported leisure outcomes or skills of the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported leisure outcomes or skills (e.g., having lots of friends, going away on a vacation, having extra time to spend with children, and so forth) of the source user 2*.

In some implementations, the acquisition operation 304 of FIG. 3 may include an operation 567 for acquiring source user data indicating one or more reported outcomes including one or more reported intellectual or academic outcomes or skills of the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported intellectual or academic outcomes or skills (e.g., achieving a certain grade point average or score on a test, increased IQ, comprehension of technically complex subject, and so forth) of the source user 2*.

In some implementations, the acquisition operation 304 of FIG. 3 may include an operation 568 for acquiring source user data indicating one or more reported outcomes including one or more reported sexual intimacy outcomes associated with the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported sexual intimacy outcomes (e.g., number of or quality of sexual encounters) associated with the source user 2*.

In some implementations, the acquisition operation 304 of FIG. 3 may include an operation 569 for acquiring source user data indicating one or more reported outcomes including one or more reported external outcomes associated with the source user as depicted in FIG. 5f. For instance, the source user data acquisition module 104* of the server 10 of FIG. 1b, the local source user device 20' of FIG. 1d, or the local end user device 30" of FIG. 1f acquiring source user data 14* indicating one or more reported outcomes including one or more reported external outcomes (e.g., subordinates' work production, behavior of others towards the source user 2*, and so forth) associated with the source user 2*.

Figure 6A:
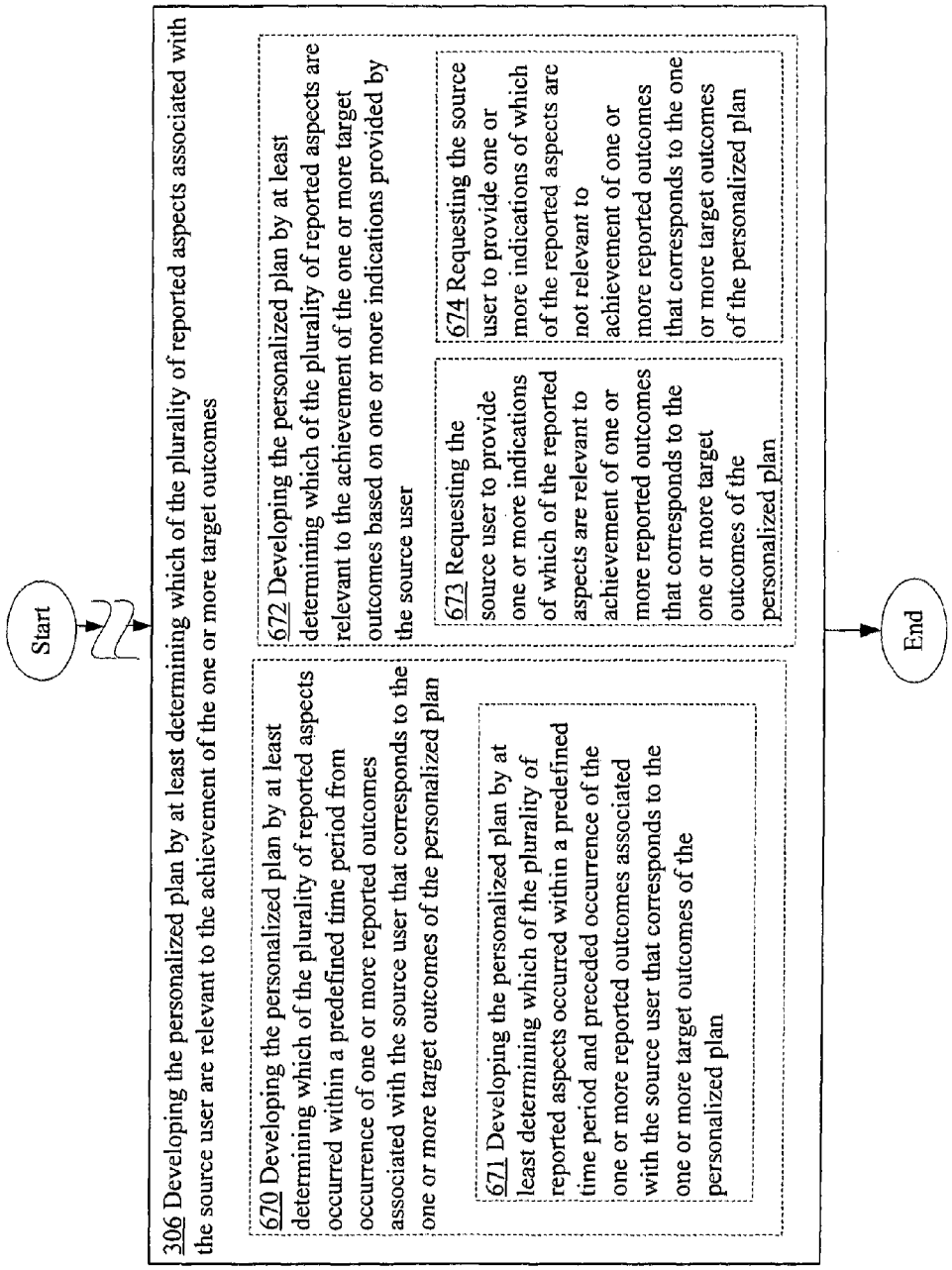
FIG. 6a is a high-level logic flowchart of a process depicting alternate implementations of the development operation 306 of FIG. 3.

Referring back to the development operation 306 of FIG. 3, in various implementations, the development operation 306 may be implemented in a variety of different ways. For example, in some implementations, the development operation 306 may include an operation 670 for developing the personalized plan by at least determining which of the plurality of reported aspects occurred within a predefined time period from occurrence of one or more reported outcomes associated with the source user that corresponds to the one or more target outcomes of the personalized plan as depicted in FIG. 6a. For instance, the personalized plan development module 106* of the server 10 of FIG. 1b, the local source user device 20' of FIG. 1d, or the local end user device 30" of FIG. 1f developing the personalized plan 16* based on the relevant reported aspect determination module 208* at least determining which of the plurality of reported aspects (e.g., as indicated by the source user data 14*) occurred within a predefined time period from occurrence of one or more reported outcomes (e.g., weight loss of 20 pounds) associated with the source user 2* (e.g., as indicated by the source user data 14*) that corresponds to the one or more target outcomes (e.g., weight loss 20 pounds) of the personalized plan 16*.

Operation 670 may, in certain implementations, include an operation 671 for developing the personalized plan by at least determining which of the plurality of reported aspects occurred within a predefined time period and preceded occurrence of the one or more reported outcomes associated with the source user that corresponds to the one or more target outcomes of the personalized plan as depicted in FIG. 6a. For instance, the personalized plan development module 106* of the server 10 of FIG. 1b, the local source user device 20' of FIG. 1d, or the local end user device 30" of FIG. 1f developing the personalized plan 16* based on the relevant reported aspect determination module 208*at least determining which of the plurality of reported aspects (e.g., as indicated by the source user data 14*) occurred within a predefined time period and preceded occurrence of the one or more reported outcomes associated with the source user 2* (e.g., as indicated by the source user data 14*) that corresponds to the one or more target outcomes of the personalized plan 16*.

In some implementations, the development operation 306 of FIG. 3 may include an operation 672 for developing the personalized plan by at least determining which of the plurality of reported aspects are relevant to the achievement of the one or more target outcomes based on one or more indications provided by the source user as depicted in FIG. 6a. For instance, the personalized plan development module 106* of the server 10 of FIG. 1b, the local source user device 20' of FIG. 1d, or the local end user device 30" of FIG. 1f developing the personalized plan 16* based on the relevant reported aspect determination module 208*at least determining which of the plurality of reported aspects (e.g., as indicated by the source user data 14*) are relevant to the achievement of the one or more target outcomes based on one or more indications provided by the source user 2*. In other words, the source user 2* may provide an indication as to which of the reported aspects may be relevant to the achievement of the one or more target outcomes of the personalized plan 16*.

In some cases, operation 672 may further include one or more additional operations. For example, in some implementations, operation 672 may include an operation 673 for requesting the source user to provide one or more indications of which of the reported aspects are relevant to achievement of one or more reported outcomes that corresponds to the one or more target outcomes of the personalized plan as depicted in FIG. 6a. For example, the reported aspect relevancy requesting module 212* of the server 10 of FIG. 1b, the local source user device 20' of FIG. 1d, or the local end user device 30" of FIG. 1f requesting the source user 2* (e.g., transmitting a request 12* via a wireless network and/or wired network 50* or indicating a request 12* via a user interface 120') to provide one or more indications of which of the reported aspects (e.g., as indicated by the acquired source user data 14*) are relevant to achievement of one or more reported outcomes (e.g., as indicated by, for example, the acquired source user data 14*) that corresponds to the one or more target outcomes of the personalized plan 16*. For these implementations, the source user 2* may be requested to merely indicate what type or types of reported aspects (e.g., reduced carbohydrate intake) may be relevant to the achievement of the one or more reported outcomes (e.g., weight loss of 30 pounds).

In some implementations, operation 672 may include an operation 674 for requesting the source user to provide one or more indications of which of the reported aspects are not relevant to achievement of one or more reported outcomes that corresponds to the one or more target outcomes of the personalized plan as depicted in FIG. 6a. For instance, the reported aspect non-relevancy requesting module 214* of the server 10 of FIG. 1b, the local source user device 20' of FIG. 1d, or the local end user device 30" of FIG. 1f requesting the source user 2* (e.g., transmitting a request 12* via a wireless network and/or wired network 50* or indicating a request 12* via a user interface 120') to provide one or more indications of which of the reported aspects (e.g., as indicated by the acquired source user data 14*) are not relevant to achievement of one or more reported outcomes (e.g., as indicated by the acquired source user data 14*) that corresponds to the one or more target outcomes of the personalized plan 16*. For these implementations, the source user 2* may be requested to merely indicate what type or types of reported aspects (e.g., getting 8 hours of sleep) may not be relevant to the achievement of the one or more reported outcomes (e.g., weight loss of 30 pounds).

Figure 6B:
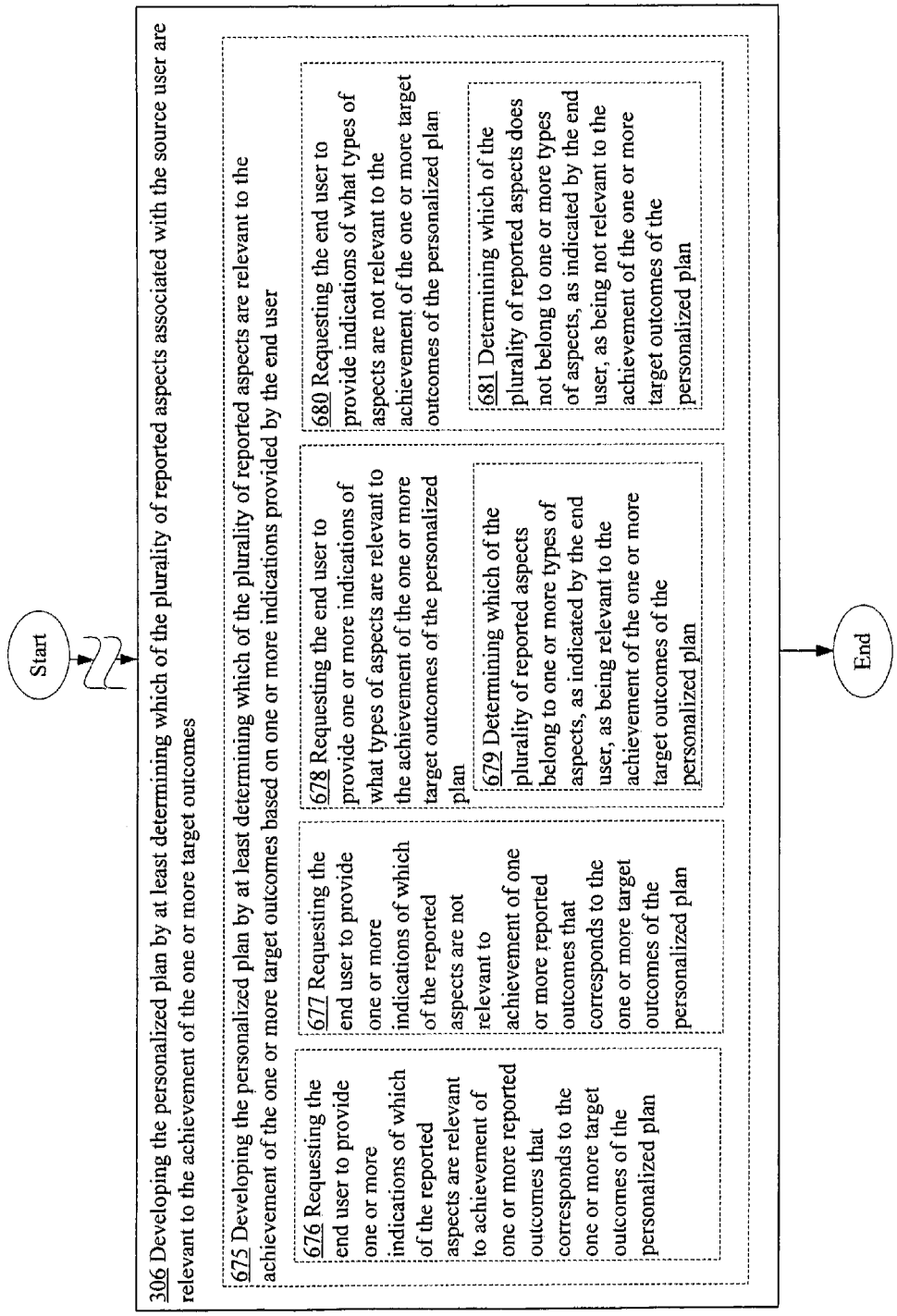
FIG. 6b is a high-level logic flowchart of a process depicting alternate implementations of the development operation 306 of FIG. 3.

In various implementations, the development of a personalized plan 16* through the development operation 306 of FIG. 3 may be based, at least in part, on input provided by an end user 4*. For example, the development operation 306 in various implementations may include an operation 675 for developing the personalized plan by at least determining which of the plurality of reported aspects are relevant to the achievement of the one or more target outcomes based on one or more indications provided by the end user as depicted in FIG. 6b. For instance, the personalized plan development module 106* of the server 10 of FIG. 1b, the local source user device 20' of FIG. 1d, or the local end user device 30" of FIG. 1f developing the personalized plan 16* as a result of the relevant reported aspect determination module 208*at least determining which of the plurality of reported aspects (e.g., as indicated by the acquired source user data 14*) are relevant to the achievement of the one or more target outcomes based on one or more indications provided by the end user 4*.

In various alternative implementations, operation 675 may further include one or more additional operations. For example, in some implementations, operation 675 may include an operation 676 for requesting the end user to provide one or more indications of which of the reported aspects are relevant to achievement of one or more reported outcomes that corresponds to the one or more target outcomes of the personalized plan as depicted in FIG. 6b. For example, the reported aspect relevancy requesting module 212* of the server 10 of FIG. 1b, the local source user device 20' of FIG. 1d, or the local end user device 30" of FIG. 1f requesting the end user 4* (e.g., transmitting a request 12* via a wireless network and/or wired network 50* or indicating a request 12* via a user interface 120") to provide one or more indications of which of the reported aspects (e.g., as indicated by the acquired source user data 14*) are relevant to achievement of one or more reported outcomes (e.g., as indicated by, for example, the acquired source user data 14*) that corresponds to the one or more target outcomes of the personalized plan 16*.

In some implementations, operation 675 may include an operation 677 for requesting the end user to provide one or more indications of which of the reported aspects are not relevant to achievement of one or more reported outcomes that corresponds to the one or more target outcomes of the personalized plan as depicted in FIG. 6b. For instance, the reported aspect non-relevancy requesting module 214* of the server 10 of FIG. 1b, the local source user device 20' of FIG. 1d, or the local end user device 30" of FIG. 1f requesting the end user 4* (e.g., transmitting a request 12* via a wireless network and/or wired network 50* or indicating a request 12* via a user interface 120") to provide one or more indications of which of the reported aspects (e.g., as indicated by the acquired source user data 14*) are not relevant to achievement of one or more reported outcomes (e.g., as indicated by, for example, the acquired source user data 14*) that corresponds to the one or more target outcomes of the personalized plan 16*.

In various implementations, operation 675 may include an operation 678 for requesting the end user to provide one or more indications of what types of aspects are relevant to the achievement of the one or more target outcomes of the personalized plan as depicted in FIG. 6b. For instance, the aspect type relevancy requesting module 216* of the server 10 of FIG. 1b, the local source user device 20' of FIG. 1d, or the local end user device 30" of FIG. 1f requesting the end user 4* (e.g., transmitting a request 12* via a wireless network and/or wired network 50* or indicating a request 12* via a user interface 120") to provide one or more indications of what types of aspects (e.g., what types of books should be read) are relevant to the achievement of the one or more target outcomes (e.g., improve reading test score) of the personalized plan 16*.

In some implementations, operation 678 may further include an operation 679 for determining which of the plurality of reported aspects belong to one or more types of aspects, as indicated by the end user, as being relevant to the achievement of the one or more target outcomes of the personalized plan as depicted in FIG. 6b. For instance, the relevant reported aspect determination module 208* of the server 10 of FIG. 1b, the local source user device 20' of FIG. 1d, or the local end user device 30" of FIG. 1f determining which of the plurality of reported aspects (e.g., as indicated by the acquired source user data 14*) belong to one or more types of aspects, as indicated by the end user 4*, as being relevant to the achievement of the one or more target outcomes of the personalized plan 16*.

In various implementations, operation 675 may include an operation 680 for requesting the end user to provide indications of what types of aspects are not relevant to the achievement of the one or more target outcomes of the personalized plan as depicted in FIG. 6b. For instance, the aspect type non-relevancy requesting module 218* of the server 10 of FIG. 1b, the local source user device 20' of FIG. 1d, or the local end user device 30" of FIG. 1f requesting the end user 4* (e.g., transmitting a request 12* via a wireless network and/or wired network 50* or indicating a request 12* via a user interface 120") to provide one or more indications of what types of aspects are relevant to the achievement of the one or more target outcomes of the personalized plan 16*.

In some implementations, operation 680 may further include an operation 681 for determining which of the plurality of reported aspects does not belong to one or more types of aspects, as indicated by the end user, as being not relevant to the achievement of the one or more target outcomes of the personalized plan as depicted in FIG. 6b. For instance, the relevant reported aspect determination module 208* of the server 10 of FIG. 1b, the local source user device 20' of FIG. 1d, or the local end user device 30" of FIG. 1f determining which of the plurality of reported aspects (e.g., as indicated by the acquired source user data 14*) does not belong to one or more types of aspects, as indicated by the end user 4*, as being not relevant to the achievement of the one or more target outcomes of the personalized plan 16*.

Figure 6C:
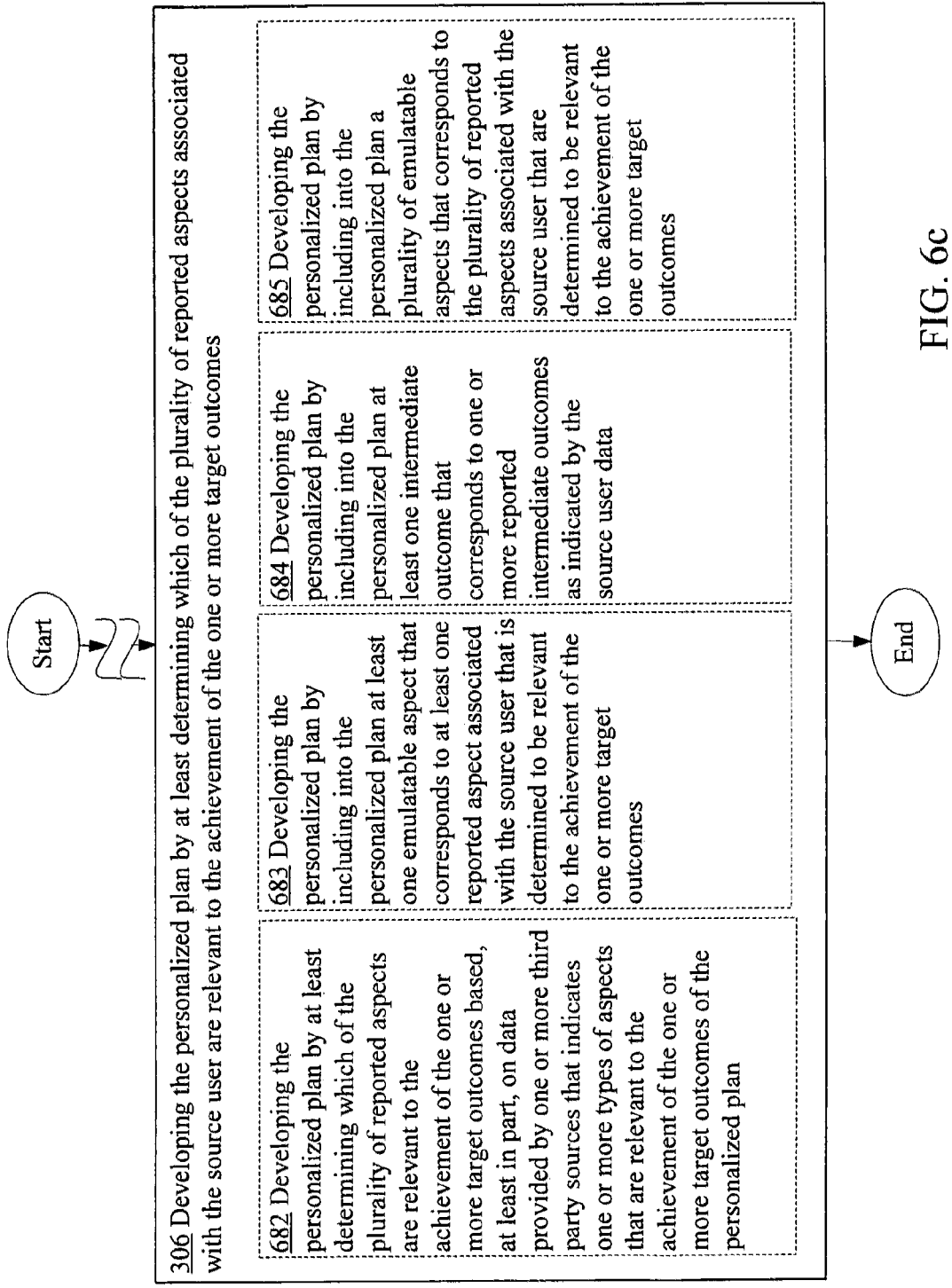
FIG. 6c is a high-level logic flowchart of a process depicting alternate implementations of the development operation 306 of FIG. 3.

In various implementations, the development operation 306 of FIG. 3 may include an operation 682 for developing the personalized plan by at least determining which of the plurality of reported aspects are relevant to the achievement of the one or more target outcomes based, at least in part, on data provided by one or more third party sources that indicates one or more types of aspects that are relevant to the achievement of the one or more target outcomes of the personalized plan as depicted in FIG. 6c. For instance, the personalized plan development module 106* of the server 10 of FIG. 1b, the local source user device 20' of FIG. 1d, or the local end user device 30" of FIG. 1f developing the personalized plan 16* as a result of the relevant reported aspect determination module 208* at least determining which of the plurality of reported aspects (e.g., as indicated by the acquired source user data 14*) are relevant to the achievement of the one or more target outcomes based, at least in part, on data provided by one or more third party sources (e.g., other source or end users 4*, publications, research papers, medical research, and so forth) that indicates one or more types of aspects that are relevant to the achievement of the one or more target outcomes of the personalized plan 16*.

In various embodiments, the development operation 306 may include an operation 683 for developing the personalized plan by including into the personalized plan at least one emulatable aspect that corresponds to at least one reported aspect associated with the source user that is determined to be relevant to the achievement of the one or more target outcomes as depicted in FIG. 6c. For instance, the personalized plan development module 106* of the server 10 of FIG. 1b, the local source user device 20' of FIG. 1d, or the local end user device 30" of FIG. 1f developing the personalized plan 16* by having the emulatable aspect inclusion module 222* include into the personalized plan 16* at least one emulatable aspect that corresponds to at least one reported aspect associated with the source user 2* that is determined to be relevant to the achievement of the one or more target outcomes of the personalized plan 16*.

In some implementations, the development operation 306 may include, in various alternative implementations, an operation 684 for developing the personalized plan by including into the personalized plan at least one intermediate outcome that corresponds to one or more reported intermediate outcomes as indicated by the source user data as depicted in FIG. 6c. For instance, the personalized plan development module 106* of the server 10 of FIG. 1b, the local source user device 20' of FIG. 1d, or the local end user device 30" of FIG. 1f developing the personalized plan 16* by having the intermediate outcome inclusion module 224* include into the personalized plan 16* at least one intermediate outcome that corresponds to one or more reported intermediate outcomes as indicated by the source user data 14*. Note that an intermediate outcome is an outcome that may precede the final reported outcome (e.g., target outcome associated with a personalized plan 16*). The intermediate outcome may be used in order to track, for example, the progress of an end user 4* in achieving a target outcome associated with a personalized plan 16*.

In some implementations, the development operation 306 may include an operation 685 for developing the personalized plan by including into the personalized plan a plurality of emulatable aspects that corresponds to the plurality of reported aspects associated with the source user that are determined to be relevant to the achievement of the one or more target outcomes as depicted in FIG. 6c. For instance, the personalized plan development module 106* of the server 10 of FIG. 1b, the local source user device 20' of FIG. 1d, or the local end user device 30" of FIG. 1f developing the personalized plan 16* by having the emulatable aspect inclusion module 222* include into the personalized plan 16* a plurality of emulatable aspects that corresponds to the plurality of reported aspects (e.g., as indicated by the acquired source user data 14*) associated with the source user 2* that are determined to be relevant to the achievement of the one or more target outcomes of the personalized plan 16*.

Figure 6D:
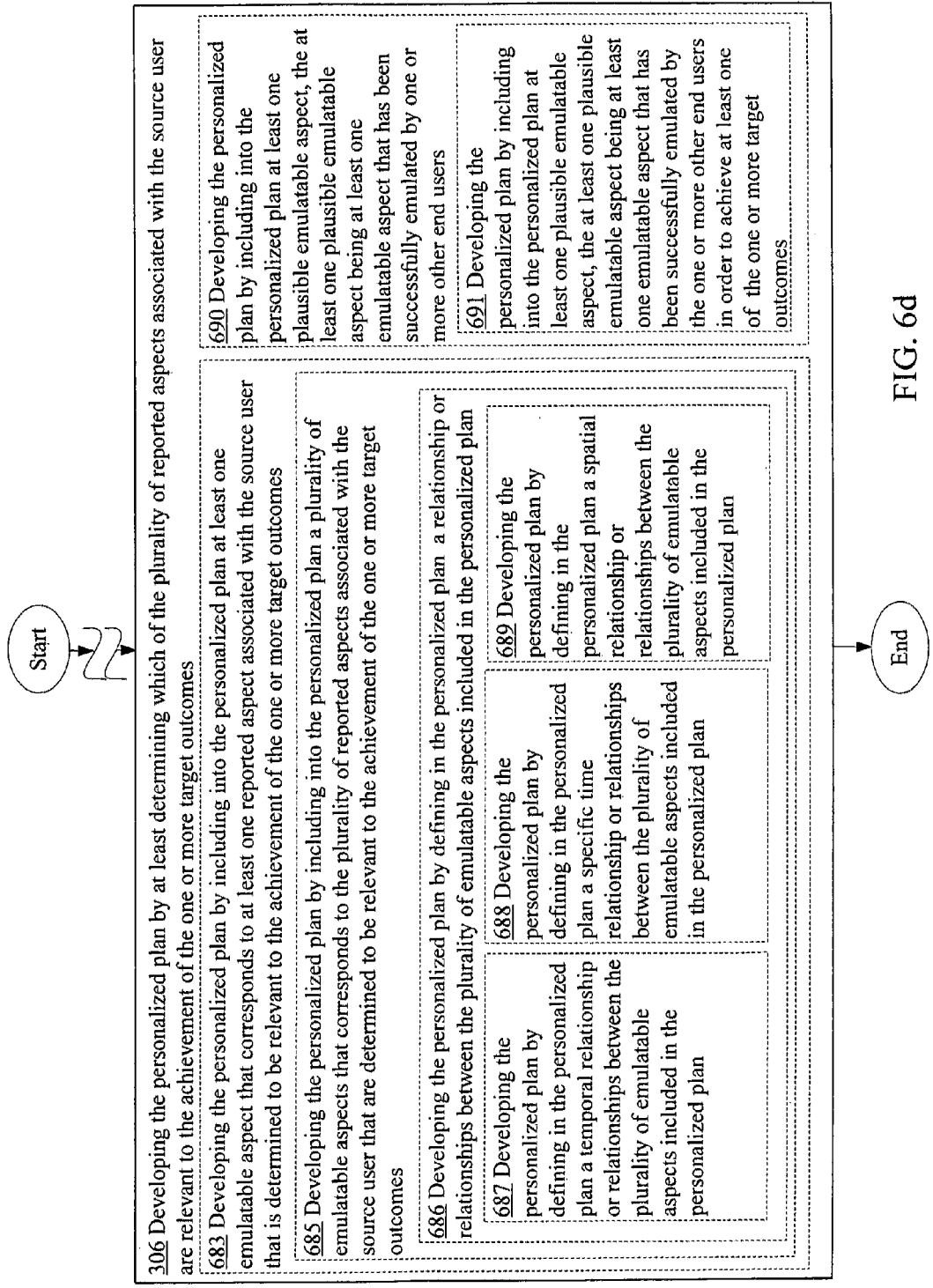
FIG. 6d is a high-level logic flowchart of a process depicting alternate implementations of the development operation 306 of FIG. 3.

Operation 685, in turn, may further include one or more additional operations as illustrated in FIG. 6d. For example, in some implementations, operation 685 may include an operation 686 for developing the personalized plan by defining in the personalized plan a relationship or relationships between the plurality of emulatable aspects included in the personalized plan. For instance, the personalized plan development module 106* of the server 10 of FIG. 1b, the local source user device 20' of FIG. 1d, or the local end user device 30" of FIG. 1f developing the personalized plan 16* by having the relationship defining module 226* define in the personalized plan 16* a relationship or relationships (e.g., temporal relationships, specific time relationships, or spatial relationships) between the plurality of emulatable aspects included in the personalized plan 16. Note that in some implementations, the personalized plan 16* may not indicate the relationships between the plurality of emulatable aspects included in the personalized plan 16*. Instead, such a personalized plan 16* may simply be a collection of emulatable aspects (as well as in some cases a collection of one or more outcomes).

In various implementations, operation 686 may further include an operation 687 for developing the personalized plan by defining in the personalized plan a temporal relationship or relationships between the plurality of emulatable aspects included in the personalized plan as depicted in FIG. 6d. For instance, the personalized plan development module 106* of the server 10 of FIG. 1b, the local source user device 20' of FIG. 1d, or the local end user device 30" of FIG. 1f developing the personalized plan 16* by having the relationship defining module 226* define in the personalized plan 16* a temporal relationship or relationships between the plurality of emulatable aspects included in the personalized plan 16*.

In some implementations, operation 686 may include an operation 688 for developing the personalized plan by defining in the personalized plan a specific time relationship or relationships between the plurality of emulatable aspects included in the personalized plan as depicted in FIG. 6d. For instance, the personalized plan development module 106* of the server 10 of FIG. 1b, the local source user device 20' of FIG. 1d, or the local end user device 30" of FIG. 1f developing the personalized plan 16* by having the relationship defining module 226* define in the personalized plan 16* a specific time relationship or relationships between the plurality of emulatable aspects included in the personalized plan 16*.

In various implementations, operation 686 may further include an operation 689 for developing the personalized plan by defining in the personalized plan a spatial relationship or relationships between the plurality of emulatable aspects included in the personalized plan as depicted in FIG. 6d. For instance, the personalized plan development module 106* of the server 10 of FIG. 1b, the local source user device 20' of FIG. 1d, or the local end user device 30" of FIG. 1f developing the personalized plan 16* by having the relationship defining module 226* define in the personalized plan 16* a spatial relationship or relationships between the plurality of emulatable aspects included in the personalized plan 16*.

In various implementations, operation 306 of FIG. 3 may include an operation 690 for developing the personalized plan by including into the personalized plan at least one plausible emulatable aspect, the at least one plausible emulatable aspect being at least one emulatable aspect that has been successfully emulated by one or more other end users as depicted in FIG. 6d. For instance, the personalized plan development module 106* of the server 10 of FIG. 1b, the local source user device 20' of FIG. 1d, or the local end user device 30" of FIG. 1f developing the personalized plan 16* by having the plausible emulatable aspect inclusion module 228* include into the personalized plan 16* at least one plausible emulatable aspect, the at least one plausible emulatable aspect being at least one emulatable aspect that has been successfully emulated by one or more other end users 4* (e.g., one or more third parties 6*).

Operation 690 may, in turn, include an operation 691 for developing the personalized plan by including into the personalized plan at least one plausible emulatable aspect, the at least one plausible emulatable aspect being at least one emulatable aspect that has been successfully emulated by the one or more other end users in order to achieve at least one of the one or more target outcomes as depicted in FIG. 6d. For instance, the personalized plan development module 106* of the server 10 of FIG. 1b, the local source user device 20' of FIG. 1d, or the local end user device 30" of FIG. 1f developing the personalized plan 16* by having the plausible emulatable aspect inclusion module 228 include into the personalized plan 16* at least one plausible emulatable aspect, the at least one plausible emulatable aspect being at least one emulatable aspect that has been successfully emulated by one or more other end users in order to achieve at least one of the one or more target outcomes of the personalized plan 16*.

Figure 7:
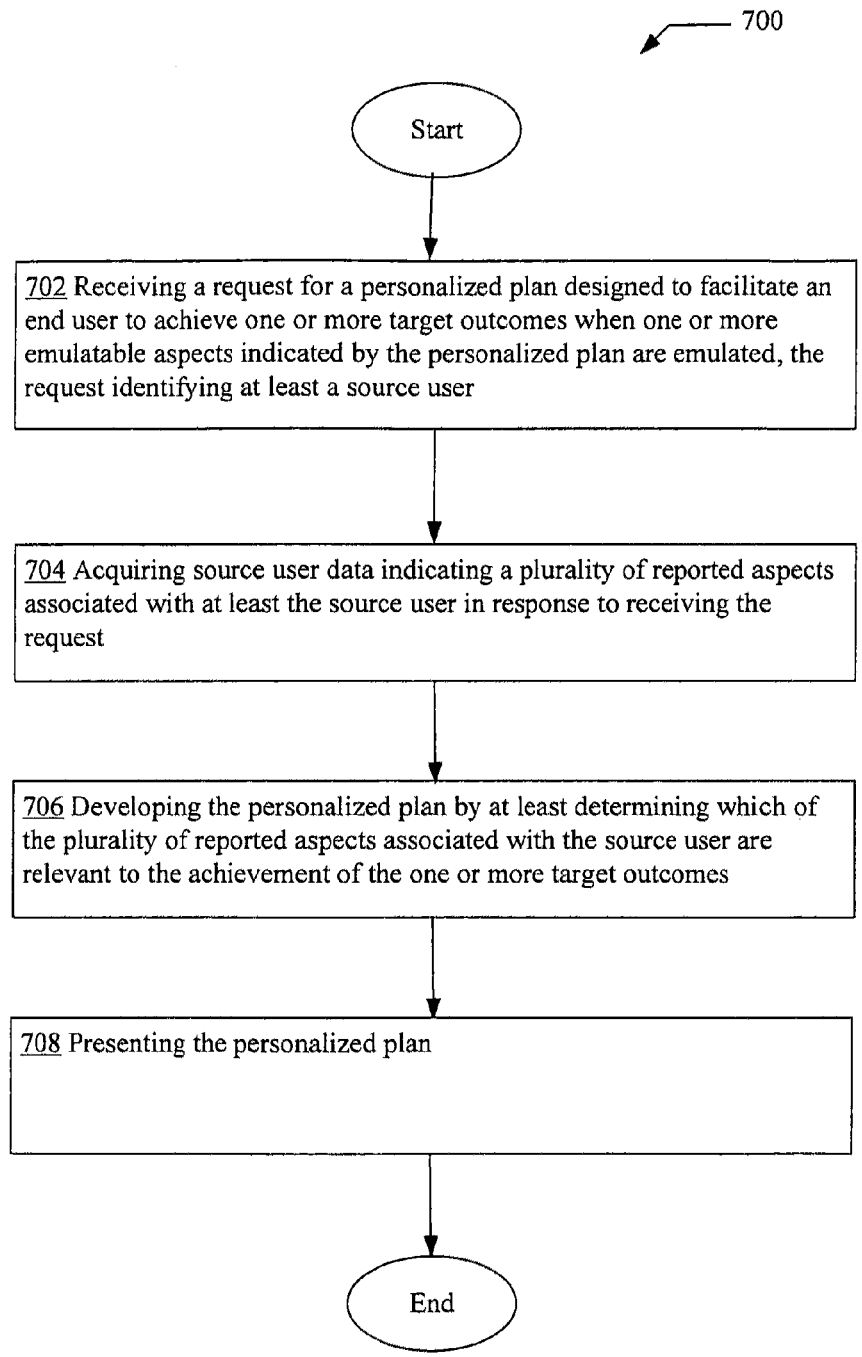
FIG. 7 is a high-level logic flowchart of another process.

Referring to FIG. 7 illustrating another operational flow 700 in accordance with various embodiments. Operational flow 700 includes certain operations that mirror the operations included in the operational flow 300 of FIG. 3. These operations include a reception operation 702, an acquisition operation 704 and a development operation 706 that corresponds to and mirror the reception operation 302, the acquisition operation 304 and the development operation 306, respectively, of FIG. 3.

In addition, operational flow 700 includes a presentation operation 708 for presenting the personalized plan as depicted in FIG. 7. For instance, the presentation module 108* of the server 10 of FIG. 1b, the local source user device 20' of FIG. 1d, or the local end user device 30" of FIG. 1f presenting (e.g., transmitting via the wireless network and/or wired network 50 or indicating via a user interface 120*) the personalized plan 16*.

In various alternative implementations, the presentation operation 708 may include one or more additional operations. For example, in some implementations, the presentation operation 708 may include an operation 893 for transmitting the personalized plan via at least one of wireless network and a wired network as depicted in FIG. 8. For instance, the transmission module 228* of the server 10 of FIG. 1b, the local source user device 20' of FIG. 1d, or the local end user device 30" of FIG. 1f transmitting the personalized plan 16* via at least one of wireless network and a wired network 50*.

In the same or different implementations, the presentation operation 708 may include an operation 894 for indicating the personalized plan via a user interface as depicted in FIG. 8. For instance, the user interface indication module 229* of the local source user device 20' of FIG. 1d or the local end user device 30" of FIG. 1f audioally or visually indicating the personalized plan 16* via a user interface 120* (e.g., a display monitor, a touchscreen, an audio system including one or more speakers, and so forth).

In the same or different implementations, the presentation operation 708 may include an operation 895 for presenting the personalized plan to the end user as depicted in FIG. 8. For instance, the presentation module 108* of the server 10 of FIG. 1b, the local source user device 20' of FIG. 1d, or the local end user device 30" of FIG. 1f presenting the personalized plan 16* to the end user 4*.

In the same or different implementations, the presentation operation 708 may include an operation 896 for presenting the personalized plan to one or more third parties as depicted in FIG. 8. For instance, the presentation module 108* of the server 10 of FIG. 1b, the local source user device 20' of FIG. 1d, or the local end user device 30" of FIG. 1f presenting the personalized plan 16* to one or more third parties 6*.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system, comprising:
   a request reception module configured to receive a request for a personalized plan indicating one or more emulatable aspects, the request identifying at least a source user and the personalized plan designed to facilitate an end user to achieve one or more target outcomes when the one or more emulatable aspects are emulated;
   a source user data acquisition module configured to acquire, in response to the request reception module receiving the request, source user data indicating a plurality of reported aspects associated with at least the source user;
   a personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
      a relevant reported aspect determination module configured to determine which of the plurality of resorted aspects occurred within a predefined time period from occurrence of one or more reported outcomes associated with the source user as indicated by the source user data and that corresponds to the one or more target outcomes of the personalized plan, wherein said relevant reported aspect determination module configured to determine which of the plurality of reported aspects occurred within a predefined time period from occurrence of one or more reported outcomes associated with the source user as indicated by the source user data and that corresponds to the one or more target outcomes of the personalized plan comprises:
         a relevant reported aspect determination module configured to determine which of the plurality of reported aspects occurred within a predefined time period and preceded occurrence of the one or more reported outcomes associated with the source user as indicated by the source user data, the one or more reported outcomes corresponding to the one or more target outcomes of the personalized plan; and
   one or more processors.

2. The system of claim 1, wherein said request reception module configured to receive a request for a personalized plan indicating one or more emulatable aspects, the request identifying at least a source user and the personalized plan designed to facilitate an end user to achieve one or more target outcomes when the one or more emulatable aspects are emulated comprises:
   a request reception module configured to receive the request for a personalized plan designed to facilitate an end user to achieve one or more target outcomes including one or more social outcomes when the one or more emulatable aspects of the personalized plan are emulated.

3. The system of claim 1, wherein said request reception module configured to receive a request for a personalized plan indicating one or more emulatable aspects, the request identifying at least a source user and the personalized plan designed to facilitate an end user to achieve one or more target outcomes when the one or more emulatable aspects are emulated comprises:
   a request reception module configured to receive the request for a personalized plan designed to facilitate an end user to achieve one or more target outcomes including one or more leisure outcomes when the one or more emulatable aspects of the personalized plan are emulated.

4. The system of claim 1, wherein said request reception module configured to receive a request for a personalized plan indicating one or more emulatable aspects, the request identifying at least a source user and the personalized plan designed to facilitate an end user to achieve one or more target outcomes when the one or more emulatable aspects are emulated comprises:
   a request reception module configured to receive the request for a personalized plan designed to facilitate an end user to achieve one or more target outcomes including one or more health or medical outcomes when the one or more emulatable aspects of the personalized plan are emulated.

5. The system of claim 1, wherein said request reception module configured to receive a request for a personalized plan indicating one or more emulatable aspects, the request identifying at least a source user and the personalized plan designed to facilitate an end user to achieve one or more target outcomes when the one or more emulatable aspects are emulated comprises:
 a request reception module configured to receive the request for a personalized plan designed to facilitate an end user to achieve one or more target outcomes including one or more subjective user states when the one or more emulatable aspects of the personalized plan are emulated.

6. The system of claim 5, wherein said request reception module configured to receive the request for a personalized plan designed to facilitate an end user to achieve one or more target outcomes including one or more subjective user states when the one or more emulatable aspects of the personalized plan are emulated comprises:
 a request reception module configured to receive the request for a personalized plan designed to facilitate an end user to achieve one or more target outcomes including one or more subjective user mental states when the one or more emulatable aspects of the personalized plan are emulated.

7. The system of claim 5, wherein said request reception module configured to receive the request for a personalized plan designed to facilitate an end user to achieve one or more target outcomes including one or more subjective user states when the one or more emulatable aspects of the personalized plan are emulated comprises:
 a request reception module configured to receive the request for a personalized plan designed to facilitate an end user to achieve one or more target outcomes including one or more subjective user physical states when the one or more emulatable aspects of the personalized plan are emulated.

8. The system of claim 5, wherein said request reception module configured to receive the request for a personalized plan designed to facilitate an end user to achieve one or more target outcomes including one or more subjective user states when the one or more emulatable aspects of the personalized plan are emulated comprises:
 a request reception module configured to receive the request for a personalized plan designed to facilitate an end user to achieve one or more target outcomes including one or more subjective user overall states when the one or more emulatable aspects of the personalized plan are emulated.

9. The system of claim 1, wherein said request reception module configured to receive a request for a personalized plan indicating one or more emulatable aspects, the request identifying at least a source user and the personalized plan designed to facilitate an end user to achieve one or more target outcomes when the one or more emulatable aspects are emulated comprises:
 a request reception module configured to receive the request for a personalized plan designed to facilitate an end user to achieve one or more target outcomes including one or more social states when the one or more emulatable aspects of the personalized plan are emulated.

10. The system of claim 1, wherein said source user data acquisition module configured to acquire, in response to the request reception module receiving the request, source user data indicating a plurality of reported aspects associated with at least the source user comprises:
 a source user data acquisition module configured to acquire the source user data indicating one or more reported aspects as at least originally reported by the source user.

11. The system of claim 1, wherein said source user data acquisition module configured to acquire, in response to the request reception module receiving the request, source user data indicating a plurality of reported aspects associated with at least the source user comprises:
 a source user data acquisition module configured to acquire the source user data indicating one or more reported aspects as at least originally reported by one or more sensors.

12. The system of claim 1, wherein said source user data acquisition module configured to acquire, in response to the request reception module receiving the request, source user data indicating a plurality of reported aspects associated with at least the source user comprises:
 a source user data acquisition module configured to acquire the source user data indicating one or more reported aspects as at least originally reported by one or more third parties.

13. The system of claim 1, wherein said source user data acquisition module configured to acquire, in response to the request reception module receiving the request, source user data indicating a plurality of reported aspects associated with at least the source user comprises:
 a source user data acquisition module configured to acquire the source user data indicating one or more reported aspects as at least originally reported via one or more social networking entries.

14. The system of claim 13, wherein said source user data acquisition module configured to acquire the source user data indicating one or more reported aspects as at least originally reported via one or more social networking entries comprises:
 a source user data acquisition module configured to acquire the source user data indicating one or more reported aspects as at least originally reported via one or more blog entries.

15. The system of claim 13, wherein said source user data acquisition module configured to acquire the source user data indicating one or more reported aspects as at least originally reported via one or more social networking entries comprises:
 a source user data acquisition module configured to acquire the source user data indicating one or more reported aspects as at least originally reported via one or more status reports.

16. The system of claim 1, wherein said source user data acquisition module configured to acquire, in response to the request reception module receiving the request, source user data indicating a plurality of reported aspects associated with at least the source user comprises:
 a source user data acquisition module configured to acquire the source user data indicating one or more user behavior incidences associated with the source user.

17. The system of claim 16, wherein said source user data acquisition module configured to acquire the source user data indicating one or more user behavior incidences associated with the source user comprises:
 a source user data acquisition module configured to acquire the source user data indicating one or more acts that were executed by the source user.

18. The system of claim 16, wherein said source user data acquisition module configured to acquire the source user data indicating one or more user behavior incidences associated with the source user comprises:

a source user data acquisition module configured to acquire the source user data indicating one or more incidences of user attitudes associated with the source user.

19. The system of claim 16, wherein said source user data acquisition module configured to acquire the source user data indicating one or more user behavior incidences associated with the source user comprises:

a source user data acquisition module configured to acquire the source user data indicating one or more incidences of user conduct associated with the source user.

20. The system of claim 1, wherein said source user data acquisition module configured to acquire, in response to the request reception module receiving the request, source user data indicating a plurality of reported aspects associated with at least the source user comprises:

a source user data acquisition module configured to acquire the source user data indicating one or more incidences of one or more beliefs associated with the source user.

21. The system of claim 1, wherein said source user data acquisition module configured to acquire, in response to the request reception module receiving the request, source user data indicating a plurality of reported aspects associated with at least the source user comprises:

a source user data acquisition module configured to acquire the source user data indicating one or more incidences of subjective user states associated with the source user.

22. The system of claim 1, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:

a relevant reported aspect determination module configured to determine, based on one or more indications provided by the source user, which of the plurality of reported aspects as indicated by the source user data are relevant to the achievement of the one or more target outcomes.

23. The system of claim 22, wherein said relevant reported aspect determination module configured to determine, based on one or more indications provided by the source user, which of the plurality of reported aspects as indicated by the source user data are relevant to the achievement of the one or more target outcomes comprises:

a reported aspect relevancy requesting module configured to request the source user to provide one or more indications of which of the reported aspects are relevant to achievement of one or more reported outcomes indicated by the source user data, the one or more reported outcomes corresponding to the one or more target outcomes of the personalized plan.

24. The system of claim 22, wherein said relevant reported aspect determination module configured to determine, based on one or more indications provided by the source user, which of the plurality of reported aspects as indicated by the source user data are relevant to the achievement of the one or more target outcomes comprises:

a reported aspect relevancy requesting module configured to request the source user to provide one or more indications of which of the reported aspects are not relevant to achievement of one or more reported outcomes indicated by the source user data, the one or more reported outcomes corresponding to the one or more target outcomes of the personalized plan.

25. The system of claim 1, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:

a relevant reported aspect determination module configured to determine, based on one or more indications provided by the end user, which of the plurality of reported aspects, as indicated by the source user data, are relevant to the achievement of the one or more target outcomes.

26. The system of claim 25, wherein said relevant reported aspect determination module configured to determine, based on one or more indications provided by the end user, which of the plurality of reported aspects, as indicated by the source user data, are relevant to the achievement of the one or more target outcomes comprises:

a reported aspect relevancy requesting module configured to request the end user to provide one or more indications of which of the reported aspects are relevant to achievement of one or more reported outcomes indicated by the source user data, the one or more reported outcomes corresponding to the one or more target outcomes of the personalized plan.

27. The system of claim 25, wherein said relevant reported aspect determination module configured to determine, based on one or more indications provided by the end user, which of the plurality of reported aspects, as indicated by the source user data, are relevant to the achievement of the one or more target outcomes comprises:

a reported aspect relevancy requesting module configured to request the end user to provide one or more indications of which of the reported aspects are not relevant to achievement of one or more reported outcomes indicated by the source user data, the one or more reported outcomes corresponding to the one or more target outcomes of the personalized plan.

28. The system of claim 25, wherein said relevant reported aspect determination module configured to determine, based on one or more indications provided by the end user, which of the plurality of reported aspects, as indicated by the source user data, are relevant to the achievement of the one or more target outcomes comprises:

an aspect type relevancy requesting module configured to request the end user to provide one or more indications of what types of aspects are relevant to the achievement of the one or more target outcomes of the personalized plan.

29. The system of claim 28, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:

a relevant reported aspect determination module configured to determine which of the plurality of reported aspects belong to one or more types of aspects indicated by the end user as being relevant to the achievement of the one or more target outcomes of the personalized plan.

30. The system of claim 25, wherein said relevant reported aspect determination module configured to determine, based on one or more indications provided by the end user, which of the plurality of reported aspects, as indicated by the source user data, are relevant to the achievement of the one or more target outcomes comprises:
    an aspect type non-relevancy requesting module configured to request the end user to provide indications of what types of aspects are not relevant to the achievement of the one or more target outcomes of the personalized plan.

31. The system of claim 30, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
    a relevant reported aspect determination module configured to determine which of the plurality of reported aspects does not belong to one or more types of aspects indicated by the end user as being not relevant to the achievement of the one or more target outcomes of the personalized plan.

32. The system of claim 1, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
    a relevant reported aspect determination module configured to determine which of the plurality of reported aspects as indicated by the source user data are relevant to the achievement of the one or more target outcomes based, at least in part, on data provided by one or more third party sources that indicates one or more types of aspects that are relevant to the achievement of the one or more target outcomes of the personalized plan.

33. The system of claim 1, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
    an emulatable aspect inclusion module configured to include into the personalized plan at least one emulatable aspect that corresponds to at least one reported aspect associated with the source user determined to be relevant to the achievement of the one or more target outcomes.

34. The system of claim 1, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
    an intermediate outcome inclusion module configured to include into the personalized plan one or more intermediate outcomes corresponding to one or more reported intermediate outcomes indicated by the source user data.

35. The system of claim 1, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
    an emulatable aspect inclusion module configured to include into the personalized plan a plurality of emulatable aspects corresponding to a plurality of reported aspects associated with the source user determined to be relevant to the achievement of the one or more target outcomes.

36. The system of claim 35, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
    a relationship defining module configured to define in the personalized plan at least one relationship between the plurality of emulatable aspects included in the personalized plan.

37. The system of claim 36, wherein said relationship defining module configured to define in the personalized plan at least one relationship between the plurality of emulatable aspects included in the personalized plan comprises:
    a relationship defining module configured to define in the personalized plan at least one temporal relationship between the plurality of emulatable aspects included in the personalized plan.

38. The system of claim 36, wherein said relationship defining module configured to define in the personalized plan at least one relationship between the plurality of emulatable aspects included in the personalized plan comprises:
    a relationship defining module configured to define in the personalized plan at least one specific time relationship between the plurality of emulatable aspects included in the personalized plan.

39. The system of claim 1, wherein said personalized plan development module including a relevant reported aspect determination module, the personalized plan development module configured to develop the personalized plan by having the relevant reported aspect determination module at least determine which of the plurality of reported aspects associated with the source user are relevant to the achievement of the one or more target outcomes comprises:
    a plausible emulatable aspect inclusion module configured to include into the personalized plan the one or more emulatable aspects including at least one plausible emulatable aspect, the at least one plausible emulatable aspect being at least one emulatable aspect that has been successfully emulated by one or more other end users.

40. The system of claim 39, wherein said plausible emulatable aspect inclusion module configured to include into the personalized plan the one or more emulatable aspects including at least one plausible emulatable aspect, the at least one plausible emulatable aspect being at least one emulatable aspect that has been successfully emulated by one or more other end users comprises:
    a plausible emulatable aspect inclusion module configured to include into the personalized plan the one or more emulatable aspects including at least one plausible emulatable aspect, the at least one plausible emulatable aspect being at least one emulatable aspect that has been successfully emulated by the one or more other end users in order to achieve at least one of the one or more target outcomes.

41. The system of claim 1, further comprising:
a presentation module configured to present the personalized plan.

42. An article of manufacture, comprising:
a non-transitory storage medium bearing:
one or more instructions for receiving a request for a personalized plan designed to facilitate an end user to achieve one or more target outcomes when one or more emulatable aspects indicated by the personalized plan are emulated, the request identifying at least a source user;
one or more instructions for acquiring source user data indicating a plurality of reported aspects associated with at least the source user in response to receiving the request; and
one or more instructions for developing the personalized plan by at least determining which of the plurality of reported aspects associated with the source user are relevant to the achievement of the one or more target outcomes, wherein said one or more instructions for developing the personalized plan by at least determining which of the plurality of reported aspects associated with the source user are relevant to the achievement of the one or more target outcomes comprises:
one or more instructions for developing the personalized plan by at least determining which of the plurality of reported aspects occurred within a predefined time period from occurrence of one or more reported outcomes associated with the source user that corresponds to the one or more target outcomes of the personalized plan, wherein said one or more instructions for developing the personalized plan by at least determining which of the plurality of reported aspects occurred within a predefined time period from occurrence of one or more reported outcomes associated with the source user that corresponds to the one or more target outcomes of the personalized plan comprises:
one or more instructions for developing the personalized plan by at least determining which of the plurality of reported aspects occurred within a predefined time period and preceded occurrence of the one or more reported outcomes associated with the source user that corresponds to the one or more target outcomes of the personalized plan.

* * * * *